US009821089B2

(12) United States Patent
Haj-Ali et al.

(10) Patent No.: US 9,821,089 B2
(45) Date of Patent: Nov. 21, 2017

(54) **COMPOSITES COMPRISING COLLAGEN EXTRACTED FROM *SARCOPHYTON SP.* CORAL**

(71) Applicant: Ramot at Tel-Aviv University Ltd., Tel-Aviv (IL)

(72) Inventors: Rami Haj-Ali, Taybe (IL); Yehuda Benayahu, Herzlia (IL); Dafna Benayahu, Herzlia (IL); Aviad Sason-Levi, Rishon-LeZion (IL); Mirit Sharabi, Ramat-Gan (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 449 days.

(21) Appl. No.: 14/376,891

(22) PCT Filed: Feb. 7, 2013

(86) PCT No.: PCT/IL2013/050119
§ 371 (c)(1),
(2) Date: Aug. 6, 2014

(87) PCT Pub. No.: WO2013/118125
PCT Pub. Date: Aug. 15, 2013

(65) Prior Publication Data
US 2015/0013299 A1    Jan. 15, 2015

Related U.S. Application Data

(60) Provisional application No. 61/637,360, filed on Apr. 24, 2012, provisional application No. 61/596,792, filed on Feb. 9, 2012.

(51) Int. Cl.
| | |
|---|---|
| *A61L 27/36* | (2006.01) |
| *A61L 27/54* | (2006.01) |
| *A61L 27/44* | (2006.01) |
| *A61L 27/48* | (2006.01) |
| *A61L 27/24* | (2006.01) |
| *D01G 1/00* | (2006.01) |
| *D01G 13/00* | (2006.01) |
| *D02G 3/02* | (2006.01) |
| *D03D 15/00* | (2006.01) |
| *D04B 1/14* | (2006.01) |
| *D04C 1/02* | (2006.01) |
| *D06M 13/00* | (2006.01) |

(52) U.S. Cl.
CPC ........... *A61L 27/3637* (2013.01); *A61L 27/24* (2013.01); *A61L 27/3687* (2013.01); *A61L 27/446* (2013.01); *A61L 27/48* (2013.01); *A61L 27/54* (2013.01); *D01G 1/00* (2013.01); *D01G 13/00* (2013.01); *D02G 3/02* (2013.01); *D03D 15/00* (2013.01); *D04B 1/14* (2013.01); *D04C 1/02* (2013.01); *D06M 13/00* (2013.01); *A61L 2430/20* (2013.01); *A61L 2430/34* (2013.01); *D10B 2211/06* (2013.01)

(58) Field of Classification Search
CPC ....... A61L 27/24; A61L 27/3637; D02G 3/02; D01G 13/00
See application file for complete search history.

(56) References Cited

U.S. PATENT DOCUMENTS

| | | | | |
|---|---|---|---|---|
| 4,474,851 A | * | 10/1984 | Urry | A61L 27/34 428/373 |
| 6,767,853 B1 | * | 7/2004 | Nakayama | D06N 3/0004 428/364 |
| 7,252,832 B1 | | 8/2007 | Stone et al. | |
| 2004/0131562 A1 | | 7/2004 | Gower et al. | |
| 2005/0271614 A1 | | 12/2005 | Wolfinbarger, Jr. | |
| 2006/0172918 A1 | | 8/2006 | Sotome et al. | |
| 2006/0210601 A1 | | 9/2006 | Yunoki et al. | |
| 2009/0287308 A1 | * | 11/2009 | Davis | A61F 2/08 623/13.12 |
| 2010/0067771 A1 | * | 3/2010 | Dahnke | A61B 6/12 382/132 |
| 2011/0038914 A1 | * | 2/2011 | Benayahu | C07K 14/78 424/423 |
| 2011/0167602 A1 | * | 7/2011 | Altman | A61F 2/08 28/165 |

FOREIGN PATENT DOCUMENTS

| | | |
|---|---|---|
| WO | WO 2009/118734 | 10/2009 |
| WO | WO 2013/118125 | 8/2013 |

OTHER PUBLICATIONS

International Preliminary Report on Patentability Dated Aug. 21, 2014 From the International Bureau of WIPO Re. Application No. PCT/IL2013/050119.
International Search Report and the Written Opinion Dated Jun. 2, 2013 From the International Searching Authority Re. Application No. PCT/IL2013/050119.
Lee et al. "Preparation and Characteristics of Hybrid Scaffolds Composed of Beta-Chitin and Collagen", Biomaterials, 25(12): 2309-2317, May 31, 2004. Abstract. Abstract, Fig.9.
Ma et al. "Collagen/Chitosan Porous Scaffolds With Improved Biostability for Skin Tissue Engineering", Biomaterials, 24: 4833-4841, Nov. 30, 2003. Abstract, p. 4835, 1-h col., Para 2-3, Fig.2, p. 4838-4839.
Manara et al. "Electrochemically-Assisted Deposition of Biomimetic Hydroxyapatite-Collagen Coatings on Titanium Plate", Inorganica Chimica Acta, 361: 1634-1645, Apr. 7, 2008. Abstract, p. 1639-1640.

(Continued)

*Primary Examiner* — Shaun R Hurley

(57) ABSTRACT

Isolated composites are disclosed comprising collagen fibers isolated from a *Sarcophyton* sp. coral. An exemplary composite comprises as a first component a bundle of collagen fibers, the collagen fibers being isolated from a *Sarcophyton* sp. coral, and a second component selected from the group consisting of a polysaccharide, a polypeptide, polylipid, a synthetic polymer, a metal and a mineral, wherein the bundle of collagen fibers comprise woven fibers, twisted fibers, braided fibers, knitted fibers, tied fibers, or sutured fibers. Uses thereof and method of generating are also disclosed.

8 Claims, 40 Drawing Sheets
(36 of 40 Drawing Sheet(s) Filed in Color)

(56) References Cited

OTHER PUBLICATIONS

Michalopoulos et al. "Development of Methods for Studying the Differentiation of Human Mesenchymal Stem Cells Under Cyclic Compressive Strain", Tissue Engineering: Part C, 18(4): 252-263, Published Online Dec. 12, 2011. p. 254.

Wang et al. "Composite Electrospun Nanomembranes of Fish Scale Collagen Peptides/Chito-Oligosaccharides: Antibacterial Properties and Potential for Wound Dressing", International Journal of Nanomedicine, 2011(6): 667-676, Apr. 1, 2011. p. 669, Figs.3, 8.

Wang et al. "Thermogelling Chitosan and Collagen Composite Hydrogels Initiated With Beta-Glycerophosphate for Bone Tissue Engineering", Biomaterials, 31(14): 3976-3985, May 31, 2010. Abstract, Figs.

\* cited by examiner

Long collagen bundles and rubber strip attached at the edge

Cable type I: long collagen fiber and rubber strip

Long collagen bundles attached at the edge

Cable type II: long collagen fiber

COMPOSITES COMPRISING COLLAGEN EXTRACTED FROM *SARCOPHYTON SP.* CORAL

RELATED APPLICATIONS

This application is a National Phase of PCT Patent Application No. PCT/IL2013/050119 having International filing date of Feb. 7, 2013, which claims the benefit of priority under 35 USC §119(e) of U.S. Provisional Patent Application No. 61/637,360 filed on Apr. 24, 2012 and U.S. Provisional Patent Application No. 61/596,792 filed on Feb. 9, 2012. The contents of the above applications are all incorporated by reference as if fully set forth herein in their entirety.

FIELD AND BACKGROUND OF THE INVENTION

The present invention, in some embodiments thereof, relates to biological composites comprising collagen and, more particularly, but not exclusively, to collagen derived from *Sarcophyton* sp. coral.

Today, the bio-medical field continues to lead and provide innovative solutions in the form of new drugs, surgical procedures and medical treatments. There are different prosthetic devices that are used in the orthopedic and cardiovascular areas. However, prosthetic materials are not biocompatible and often lead to acute to chronic rejection. The recent advances technology of scaffold constructs and new biocompatible material implementations are aimed at providing solutions to the short comings of medical prosthetic devices. Computer simulations of advanced composite materials have also found their path in new design of composite materials and structures for a variety of engineering applications.

Bio-compatible and hybrid composite material and structural devices made from synthetic and natural materials have great potential for damage repair of critical systems in the human body, such as heart valves, vessels, spine discs, ligaments, among others.

Collagens are the main structural proteins responsible for the structural integrity of vertebrates and many other multicellular organisms.

Collagen provides biomaterials for a myriad of uses including pharmaceutical (haemostatic compresses, sponges, dressings in particular healing dressings), medical (prostheses such as cardiac valves, tendons and ligaments, skin substitutes, filling agents), odontological (gum implants) and cosmetic (additive, anti-wrinkling agent, microcontainer for perfumed substances). Collagen-based products can be made into membranes, films, sheets, sponges and dispersions of fibrils for any of the above purposes.

The use of animal-derived collagen is problematic due to the possible risks of contamination by non-conventional infectious agents. While the risks raised by bacterial or viral contamination can be fully controlled, prions are less containable and present considerable health risks. These infectious agents, which appear to have a protein-like nature, are involved in the development of degenerative animal encephalopathy (sheep trembling disease, bovine spongiform encephalopathy) and human encephalopathy (Creutzfeld-Jacob disease, Gerstmann-Straussler syndrome, and kuru disease). Due to the lengthy time before onset of the disease, formal controls are difficult to conduct.

The use of animal collagen is further exacerbated due to species differences. In addition, allergic reactions to animal collagen have been documented. Collagen, extracted from either animal or human cadavers, has typically undergone irreversible crosslinking and harsh processing methods, both of which compromise its biological and mechanical functions.

U.S. Patent Application Publication No. 20050271614 teaches use of collagen of aquatic origin for cosmetic, pharmacological, dental, and cell culture products.

U.S. Patent Application Publication No. 20060210601 teaches a processed (non-native) collagen of enhanced elasticity and mechanical endurability.

WO 2009/118734 teaches the use of collagen derived from *Sarcophyton* sp. coral.

SUMMARY OF THE INVENTION

According to an aspect of some embodiments of the present invention there is provided an isolated composite comprising as a first component a bundle of collagen fibers, the collagen fibers being isolated from a *Sarcophyton* sp. coral, and a second component selected from the group consisting of a polysaccharide, a polypeptide, polylipid, a synthetic polymer, a metal and a mineral, wherein the bundle of collagen fibers comprise woven fibers, twisted fibers, braided fibers, knitted fibers, tied fibers, or sutured fibers.

According to an aspect of some embodiments of the present invention there is provided a wire composed of the composite described herein.

According to an aspect of some embodiments of the present invention there is provided a wire comprising a bundle of collagen fibers, the collagen fibers being isolated from a *Sarcophyton* sp. coral, wherein the bundle of collagen fibers comprise woven fibers, twisted fibers, braided fibers, knitted fibers, tied fibers, or sutured fibers.

According to an aspect of some embodiments of the present invention there is provided an isolated composite comprising, as a first component, collagen fibers extracted from a *Sarcophyton* sp. coral and a second component selected from the group consisting of an alginate, agar, a non-coral collagen, a chitosan and a synthetic polymer.

According to an aspect of some embodiments of the present invention there is provided an isolated composite comprising, as a first component, a plurality of collagen fibers wherein a length of each of the collagen fibers is between 2 mm-10 mm, the collagen being isolated from a *Sarcophyton* sp. coral; and a second component selected from the group consisting of a polysaccharide, a polypeptide, a polylipid, a metal, a synthetic polymer and a mineral.

According to an aspect of some embodiments of the present invention there is provided a method of generating a collagen composite comprising:

(a) cutting the collagen fiber of the *Sarcophyton* sp. coral to generate cut collagen fibers of a length between 2 mm-10 mm; and (b) contacting the cut collagen fibers with the second component, thereby generating the collagen composite.

According to an aspect of some embodiments of the present invention there is provided a method of generating a collagen composite comprising:

(a) manipulating the collagen fibers of the *Sarcophyton* sp. coral to generate a bundle of collagen fibers; and (b) contacting the bundle of collagen fibers with the second component, thereby generating the collagen composite.

According to an aspect of some embodiments of the present invention there is provided a method of generating a collagen composite, the composite comprising, as a first component, collagen fibers extracted from a *Sarcophyton* sp. coral and a second component selected from the group consisting of an alginate, agar, a non-coral collagen, a chitosan and a synthetic polymer, comprising contacting the collagen fibers with the second component, thereby generating the collagen composite.

According to an aspect of some embodiments of the present invention there is provided an implantable device comprising the composite described herein.

According to an aspect of some embodiments of the present invention there is provided an implantable device comprising the wire described herein.

According to some embodiments of the invention, wherein each of the collagen fibers are aligned in a single direction with respect to each other.

According to some embodiments of the invention, the synthetic polymer is selected from the group consisting of polyurethane, polyester and epoxy.

According to some embodiments of the invention, each of the collagen fibers are aligned in a single direction with respect to each other.

According to some embodiments of the invention, the collagen fibers are non-aligned in a single direction with respect to each other.

According to some embodiments of the invention, the polysaccharide is selected from the group consisting of alginate, agar, hyaluronic acid, chitin, glycogen, chitosan, carboxymethylcellulose starch, cellulose, pectin, gellan, gums and modified starch.

According to some embodiments of the invention, the polypeptide is selected from the group consisting of silk, elastin, fibronectin, fibrin, fibrinogen and a non-coral collagen.

According to some embodiments of the invention, the metal is selected from the group consisting of platinum, titanium and stainless steel.

According to some embodiments of the invention, the collagen fibers are embedded in a matrix of said second component.

According to some embodiments of the invention, the collagen fibers are selected from the group consisting of woven fibers, twisted fibers, braided fibers, knitted fibers, tied fibers and sutured fibers.

According to some embodiments of the invention, the synthetic polymer is selected from the group consisting of poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolid-es) (PLGA), polyanhydrides, and polyorthoesters.

According to some embodiments of the invention, the mineral is selected from the group consisting of calcium, magnesium, boron, zinc, copper, manganese, iron, silicon, selenium, sodium, potassium, phosphorus and sulfur.

According to some embodiments of the invention, at least a portion of the first component and a portion of the second component are crosslinked.

According to some embodiments of the invention, the manipulating is selected from the group consisting of weaving, twisting, braiding, knitting, tying and suturing.

According to some embodiments of the invention, the method further comprises crosslinking the composite following the contacting.

According to some embodiments of the invention, the method further comprises freeze-drying the composite following the contacting.

According to some embodiments of the invention, the implantable device further comprises a bioactive agent selected from the group consisting of antimicrobials, antibacterials, anti-fungals, antibiotics, anti-viral agents, analgesics, anti-adhesives, anesthetics, anti-inflammatories, antispasmodics, hormones, growth factors, muscle relaxants, antineoplastics, immunogenic agents, immunosuppressants, steroids, lipids, narcotics, lipopolysaccharides, polysaccharides, polypeptides, enzymes, and combinations thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a photograph of an agar hydrogel reinforced with long, soft coral collagen fibers prior to tensile loading. Black carbon particles were sprayed on the surface of the film in order to use optical image acquisition and track the displacement of the deformed material.

FIG. 2 is a photograph of an agar hydrogel reinforced with long soft coral collagen fibers under tensile loading. The hydrogel material yielded under the applied load while the fibers continued to carry added loads.

FIG. 3 is a photograph of the "Digital Image Correlation" results for an agar hydrogel reinforced with long soft coral collagen fibers subjected to axial tension. The displacement field illustrates a linear deformation in the solidified film under tension.

FIG. 4 is a photograph of an agar hydrogel reinforced with long soft collagen fibers following a tensile test. The hydrogel yielded under the applied loading while the collagen fibers continued to carry additional loads.

Figure 5:
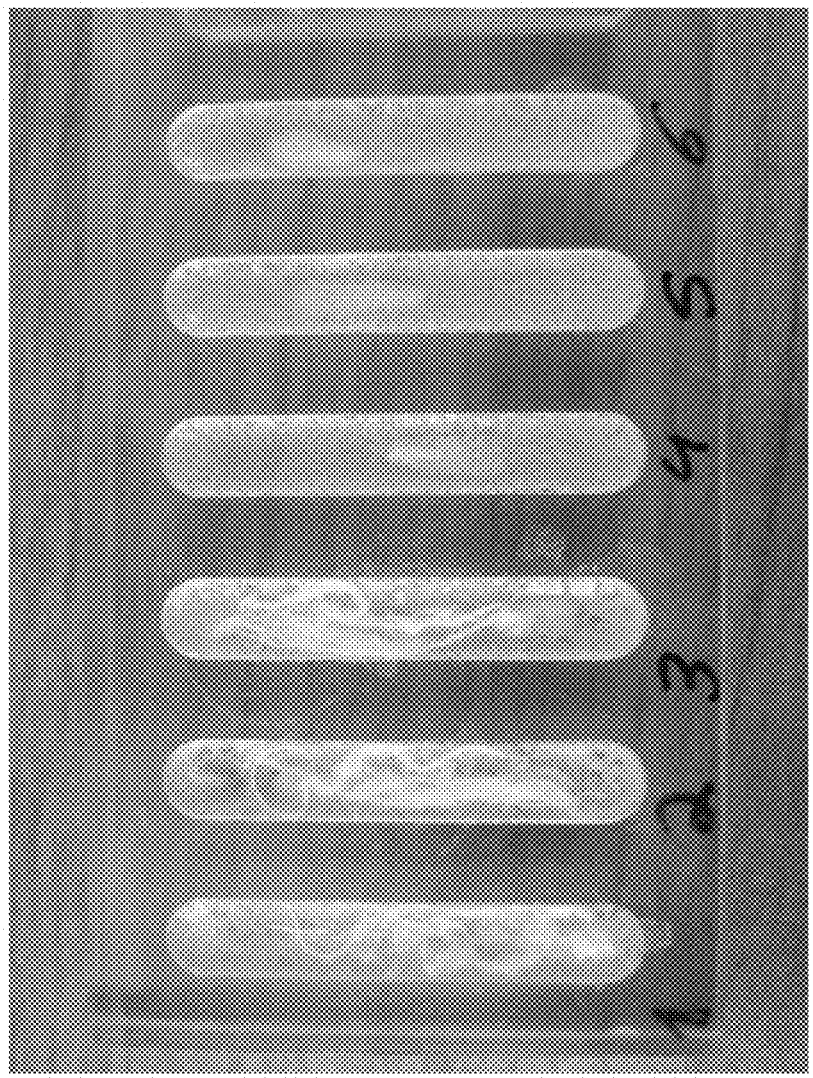

FIG. 5 is a photograph of a mold used to construct different collagen composite samples and control their geometry. The figure shows six samples with the same geometry. The first three samples (1-3) are made from soft coral collagen fibers or bundles with a collagen (short fibers)

matrix binder. The other three (4-6) samples are collagen matrix with short fibers used for control.

Figure 6:
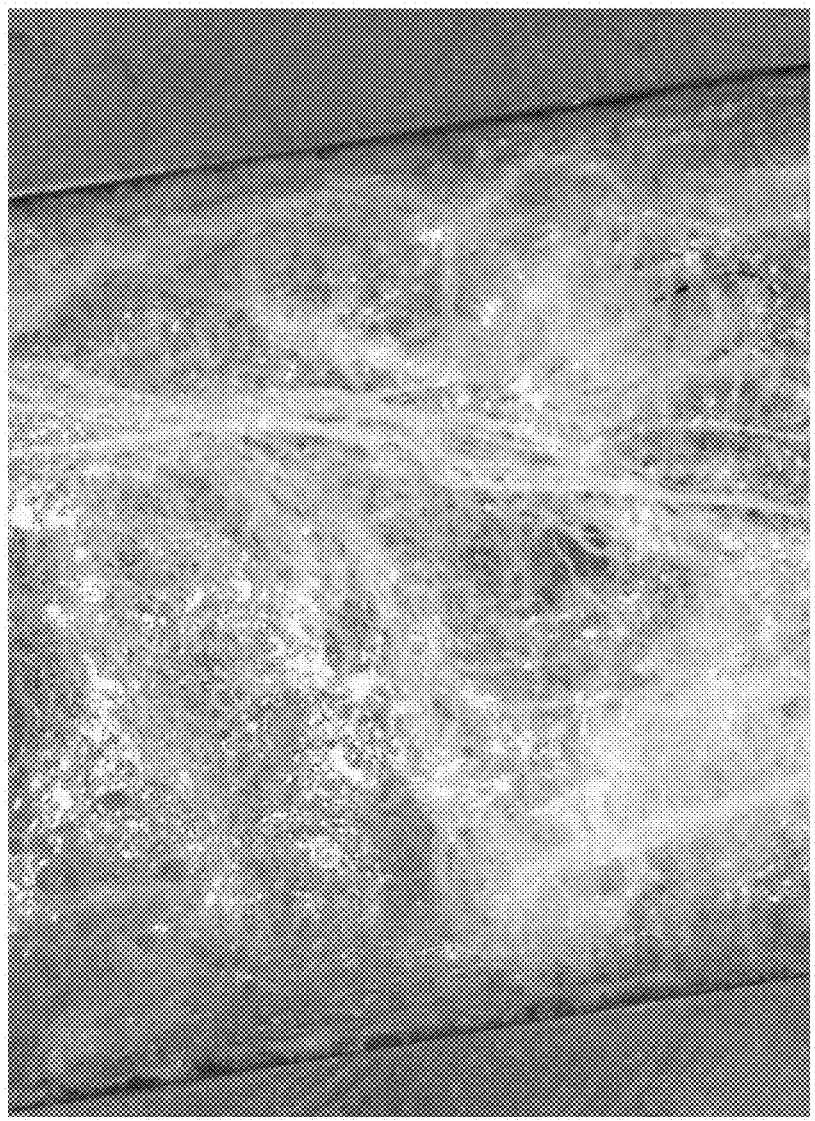

FIG. 6 is a photograph of a dehydrated sample of long soft coral collagen fibers (white) in a matrix of short collagen fibers (clear) originating from animal source.

Figure 7:
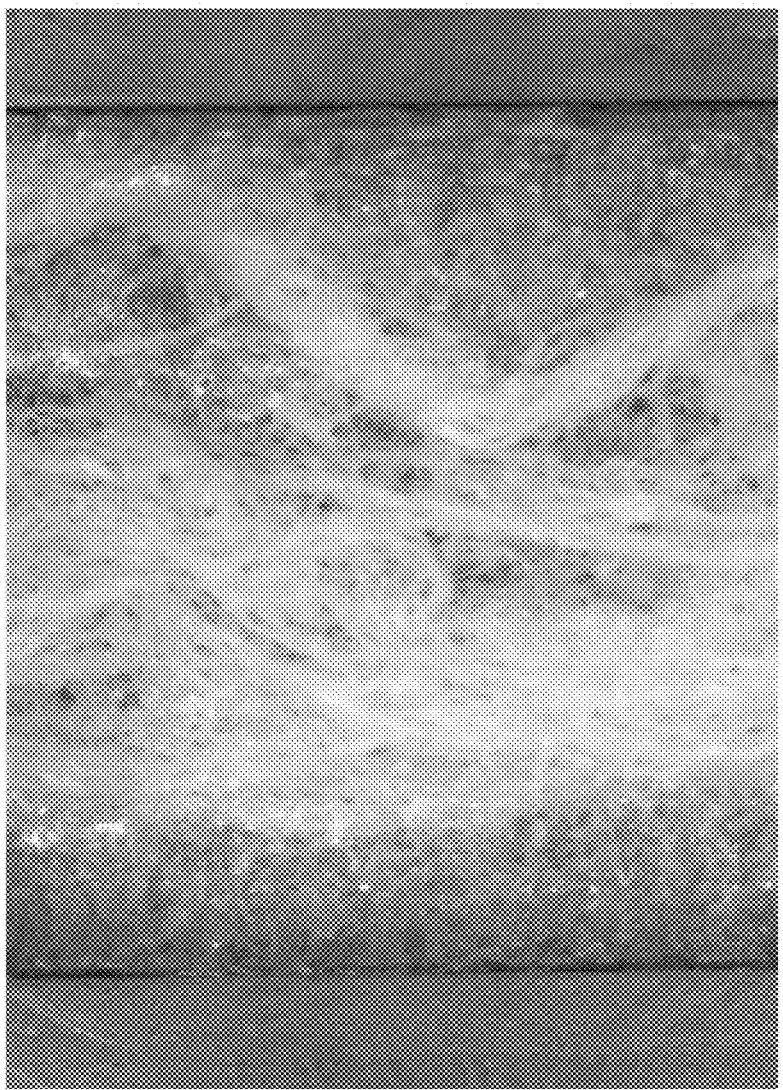

FIG. 7 is a photograph of a dehydrated sample of long soft coral collagen bundles (white) in a matrix of short collagen fibers (clear) originating from animal source.

Figures 8A, 8B:
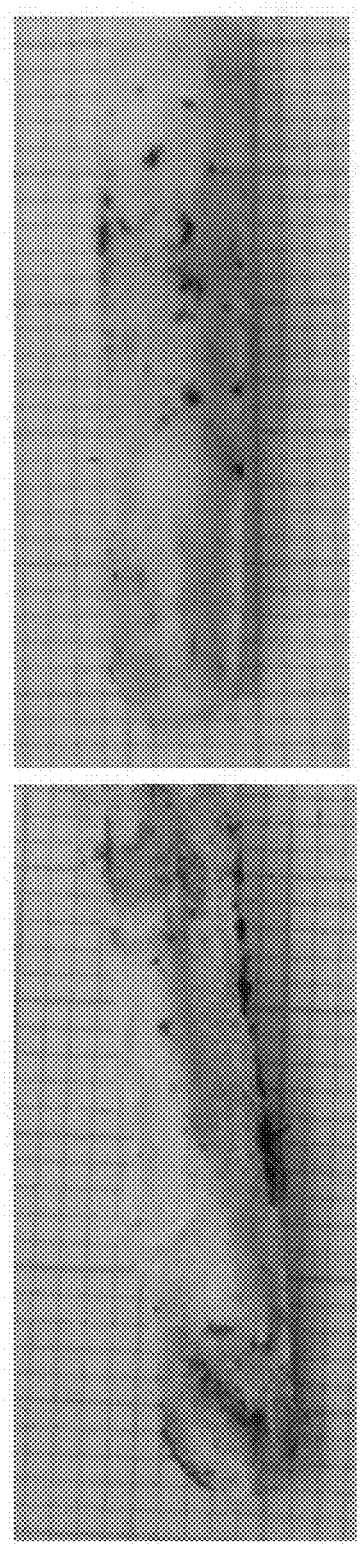

FIGS. 8A-B are photographs of trips of collagen matrix from animal source (porcine). (A) With soft coral long collagen-fibers reinforcement embedded mechanically and chemically cross-linked; (B) without reinforcement.

Figure 9:
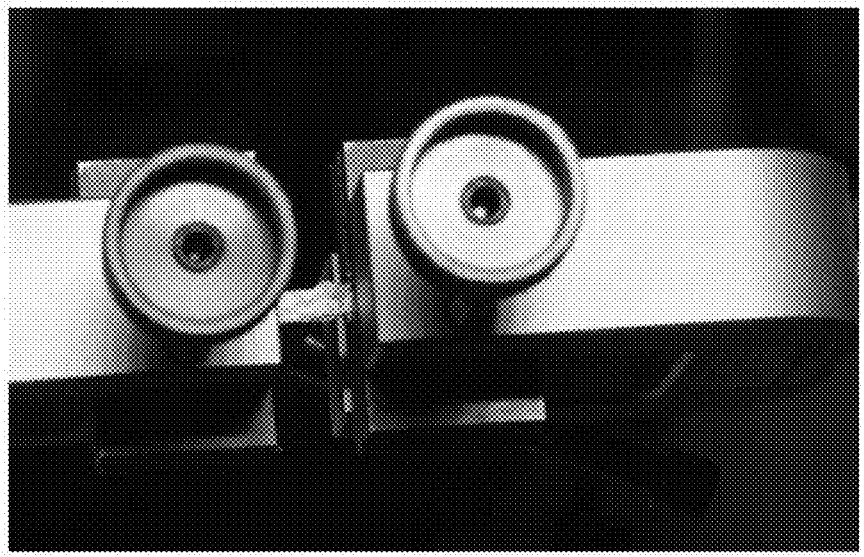

FIG. 9 is a photograph of strips of composite collagen matrix reinforced with long collagen fibers stretched uniaxially in the fiber direction.

Figure 10:
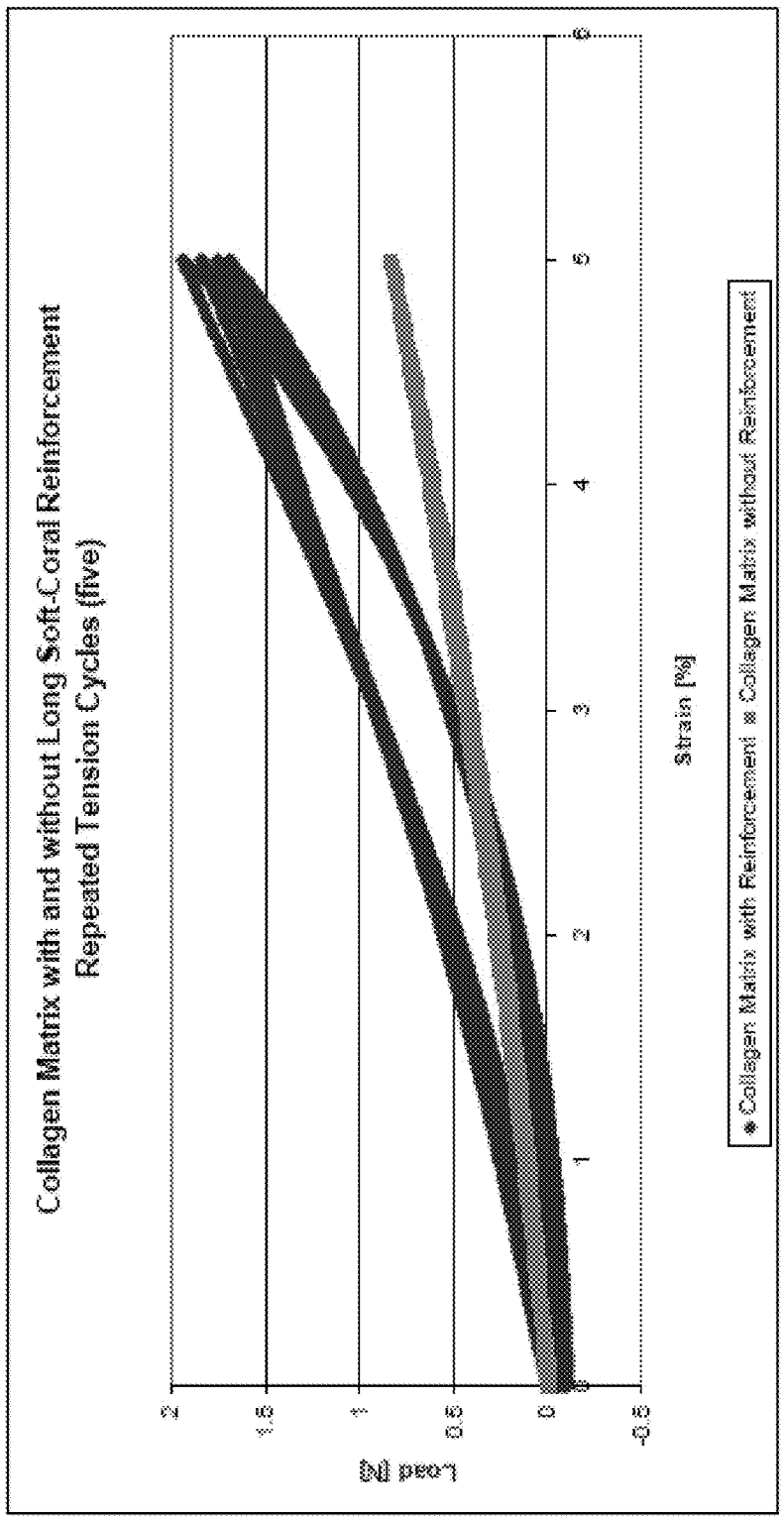

FIG. 10 is a graph illustrating load-strain mechanical performance of two strips of composite collagen-matrix reinforced with long-collagen fibers stretched uniaxially in the fiber direction. The reinforcement of highly-elastic long collagen fibers contribute to a hysteretic behavior and stiffness but with hyperelastic behavior similar to soft tissue. The matrix-alone strip has more linear behavior and has less hyperelastic performance.

Figure 11:
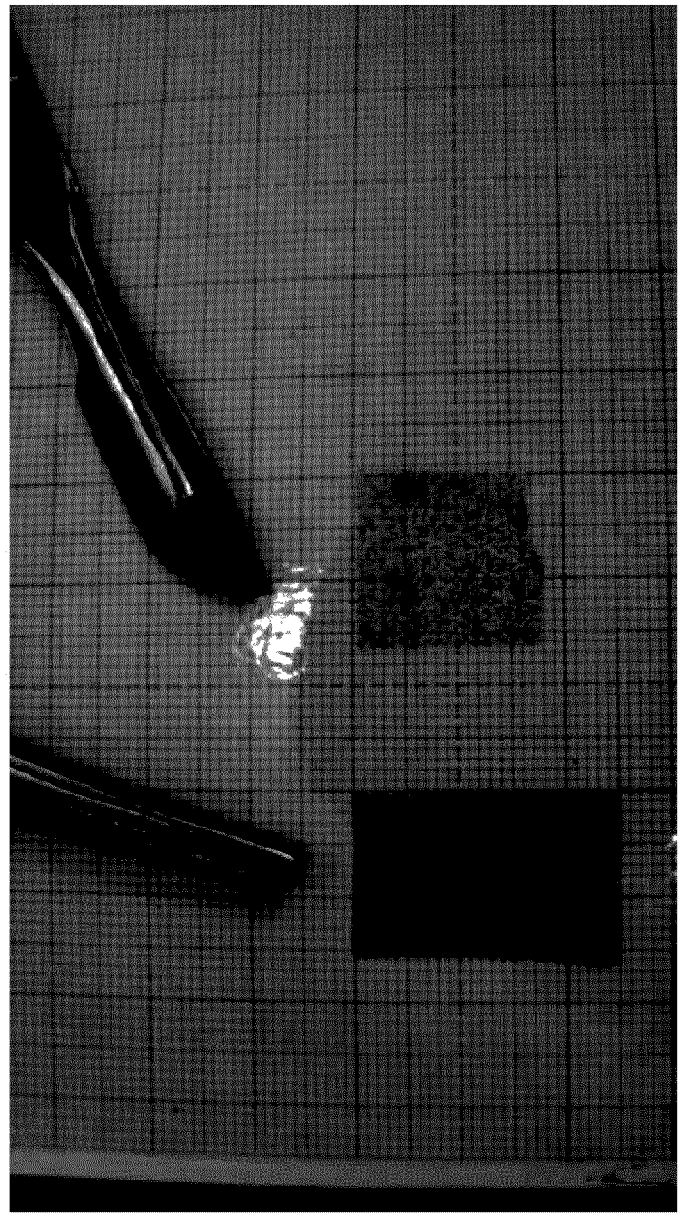

FIG. 11 is a photograph of soft coral collagen fibers embedded in a polymeric matrix (left) and a control sample in the form of a pure polymeric film.

Figure 12:
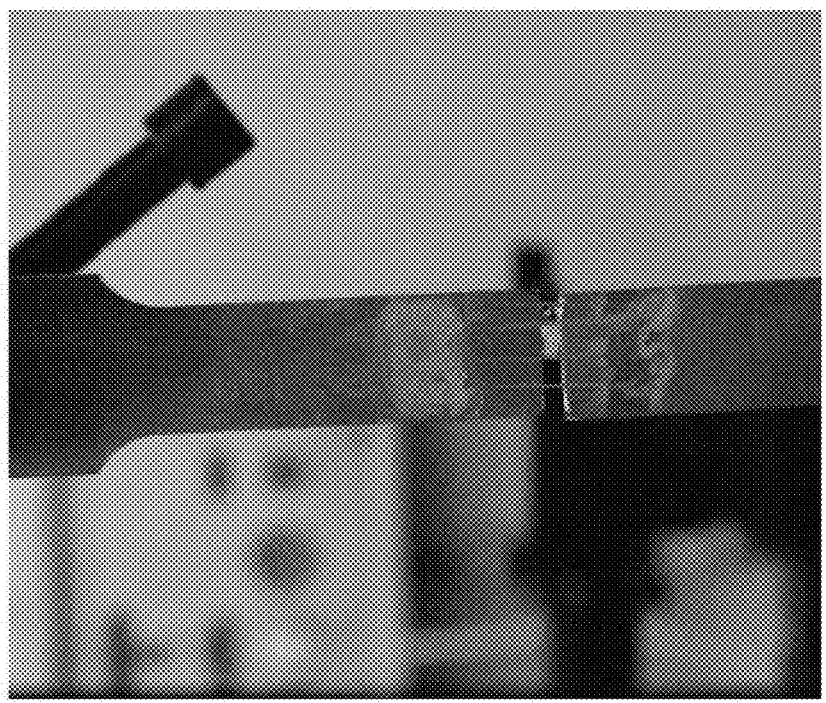

FIG. 12 is a photograph of twisted strands of long soft coral collagen fibers forming four composite wires. The assembly of wires were glued and stretched to examine their elastic mechanical behavior.

Figure 13:
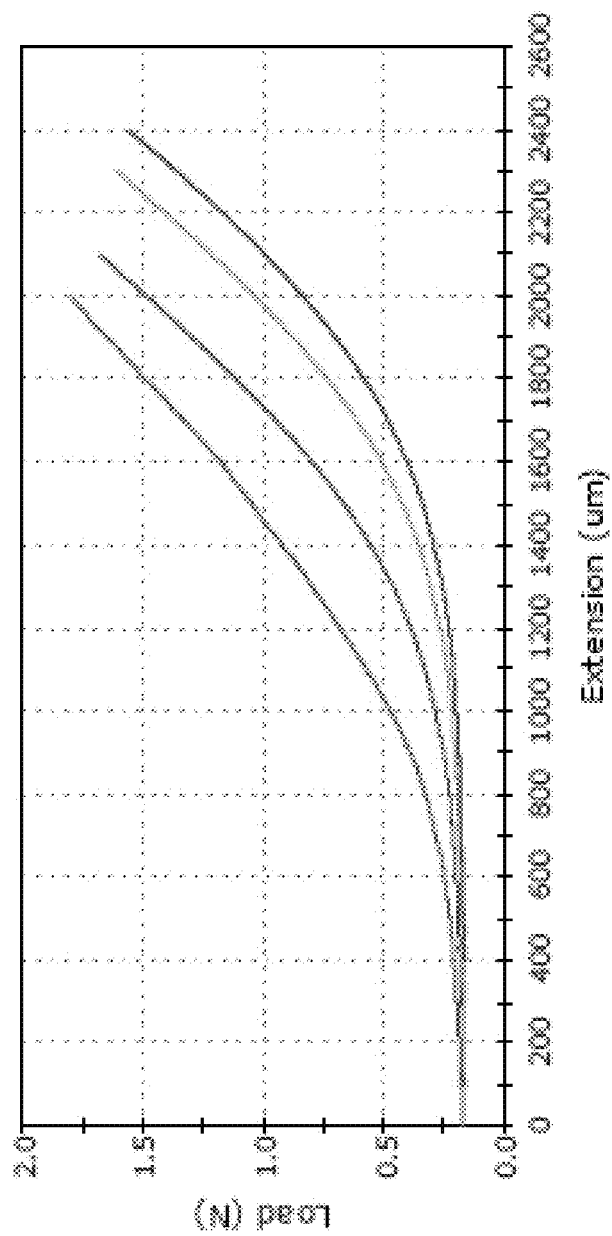

FIG. 13 is a graph illustrating load versus stretch curves for four soft coral collagen long fiber bundles subjected to uniaxial loading. The bundles were cut to initial length of 10 mm. Repeated cycles of uniaxial stretch were performed up to 20%. All four fiber bundles withstood this level of stretch. All curves need to be shifted and their origin is aligned when the load is above zero (0.16N).

FIGS. 14A-D are photographs illustrating the stages of wire or cable formation.

Figure 14B:
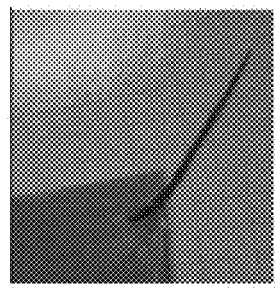
Figure 14D:
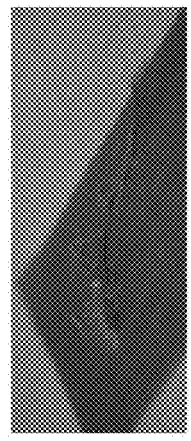
Figure 14A:
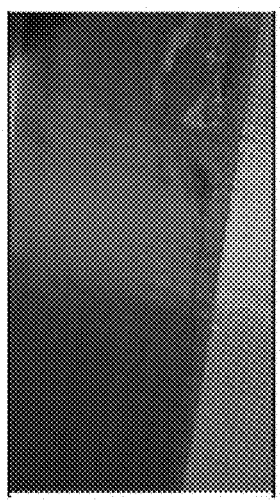
Figure 14C:
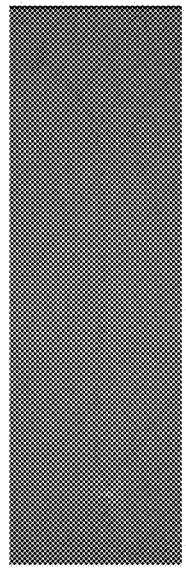
Figure 14F:
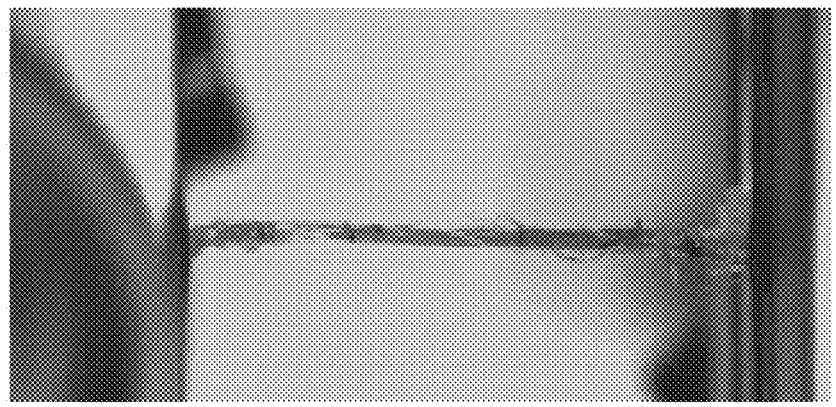
Figure 14E:
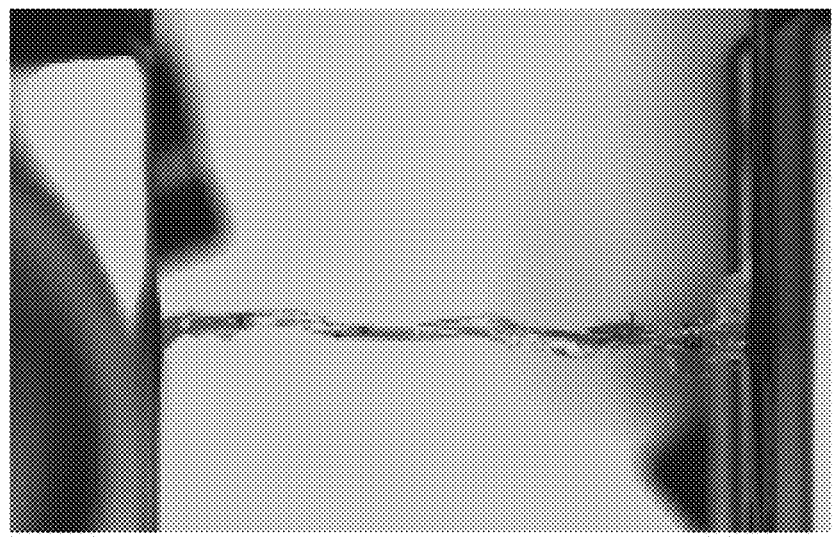

FIGS. 14E-F are photographs illustrating mechanical testing of cable type one. E—During the tension test, the rubber band twisted as a result of the long collagen fibers' orientation. F—prior to the tension test.

Figure 14H:
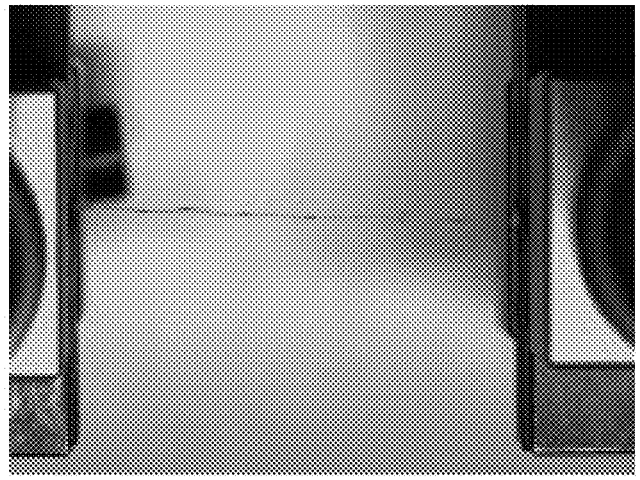
Figure 14G:
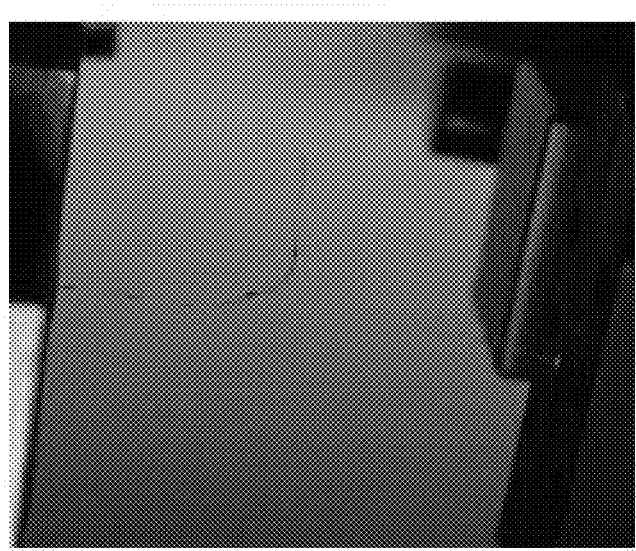

FIGS. 14G-H are photographs illustrating mechanical testing of cable type two. G—After the tension test. H—during the tension test.

Figure 14I:
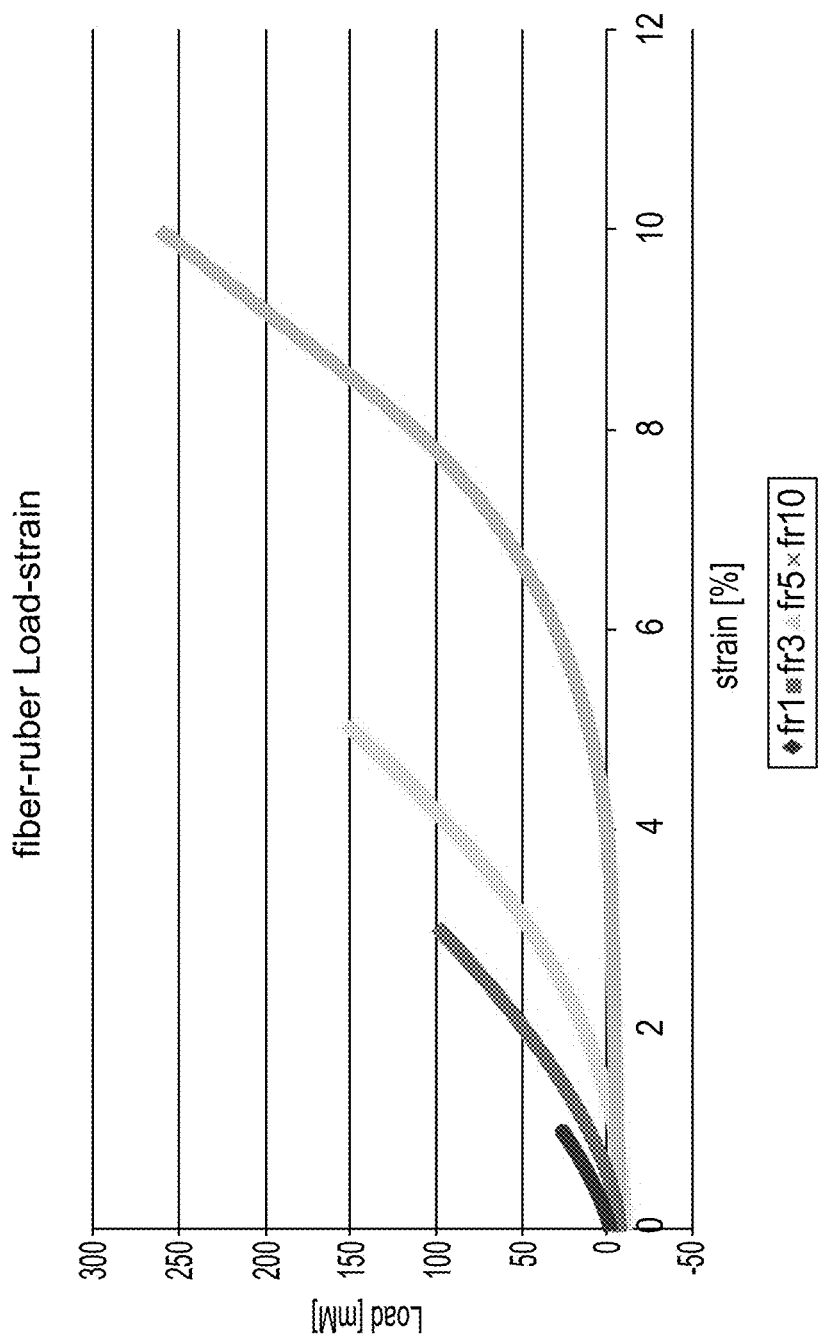

FIG. 14I is a graph illustrating load versus stretch curves for cable type one.

Figure 14J:
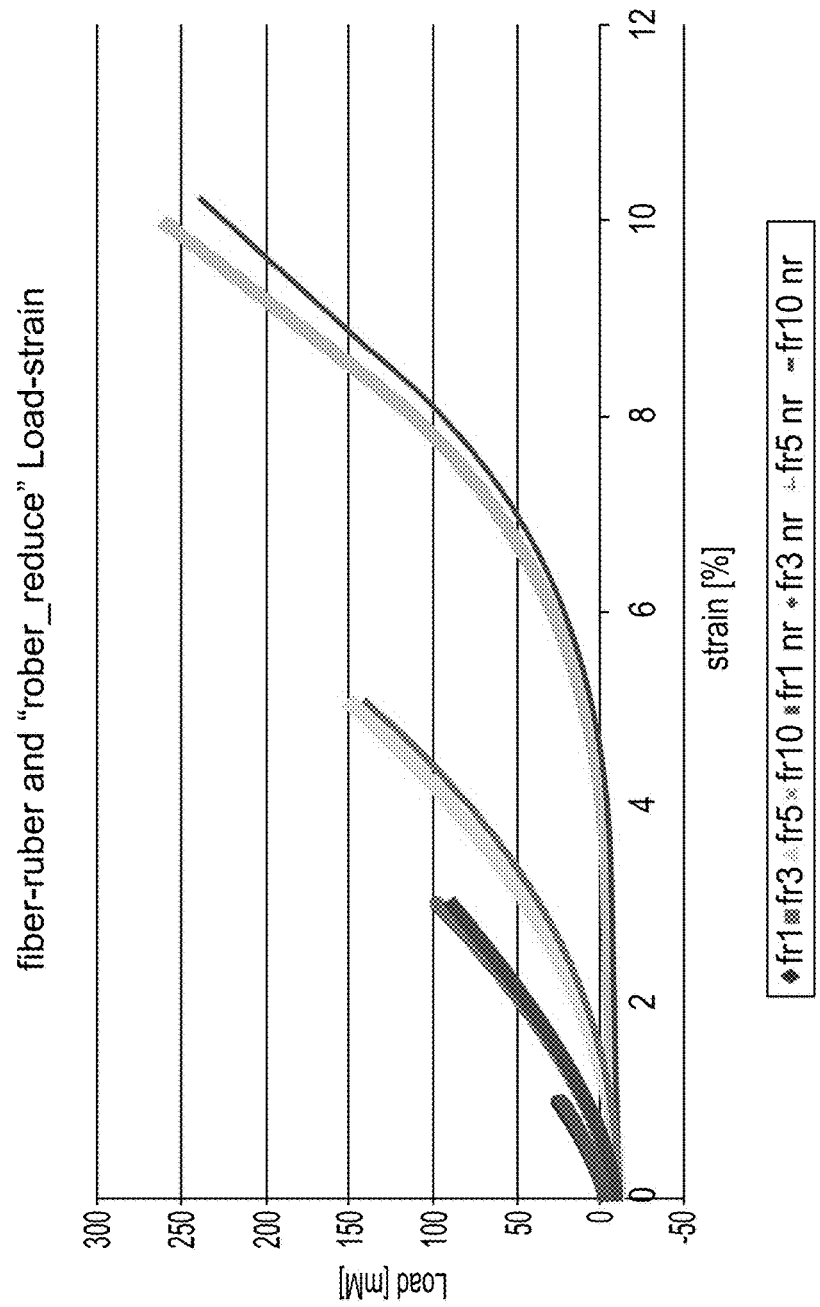

FIG. 14J is a graph illustrating load versus stretch curves for cable type one with the effect of the rubber contribution to load-displacement curve shown comparative to original.

Figure 14K:
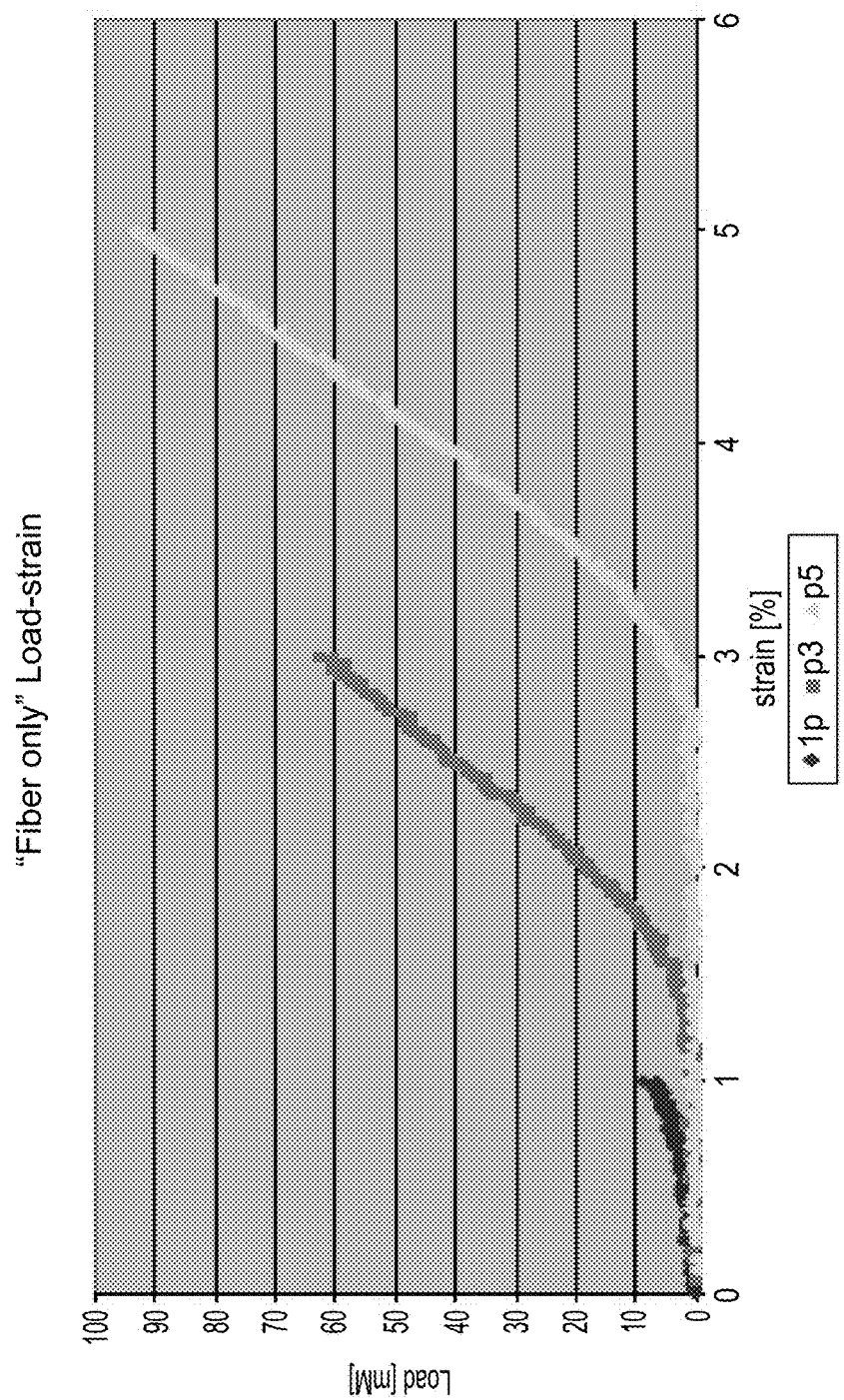

FIG. 14K is a graph illustrating load versus stretch curves for cable type one.

Figure 14L:
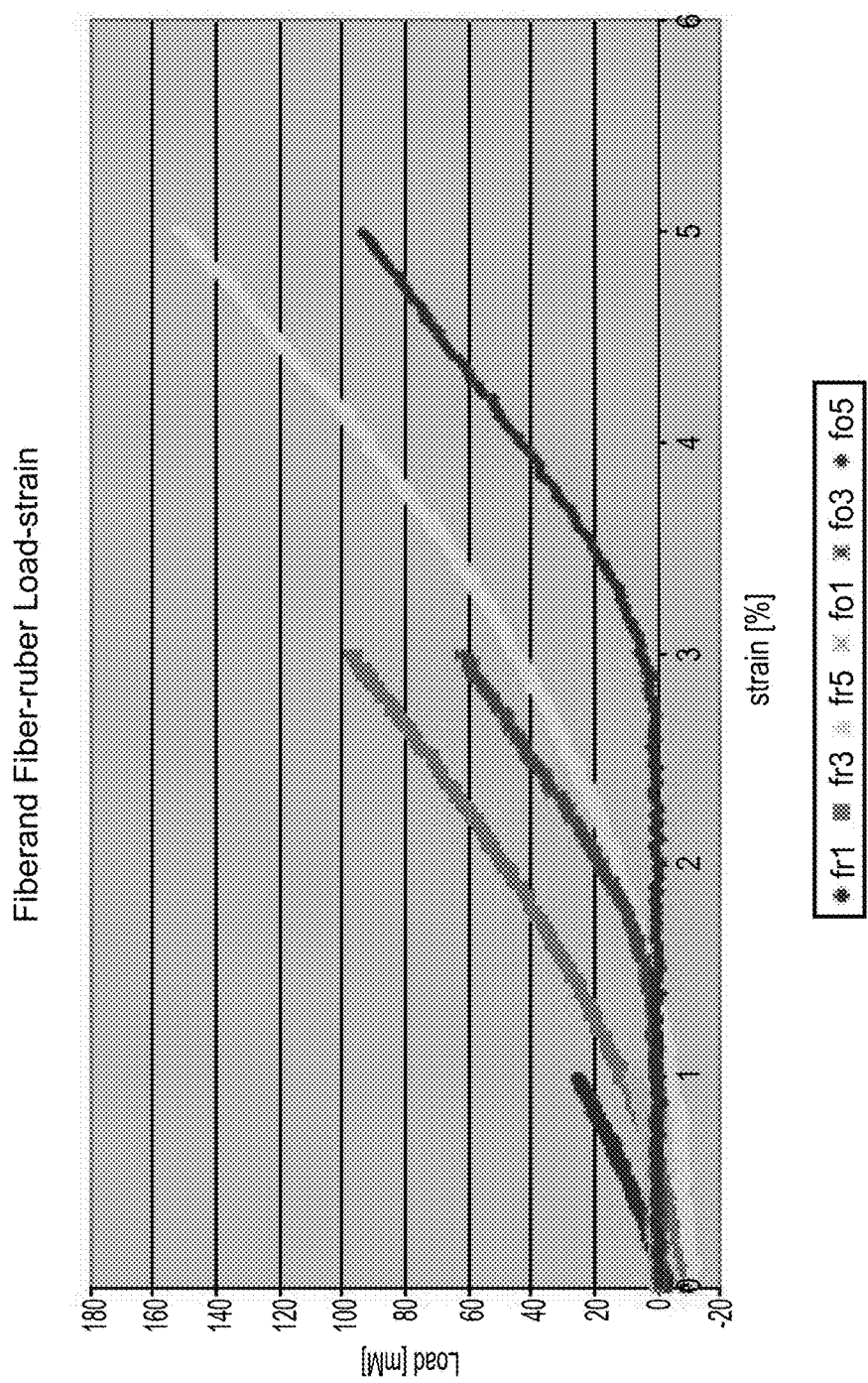

FIG. 14L is a graph illustrating load versus stretch curves for cable type two with the effect of the rubber contribution to load-displacement curve shown comparative to original.

Figure 14M:

FIG. 14M is a photograph of soft coral long collagen fibers collected as braided bundles to form a long composite wire. The wire was placed in a uniaxial mechanical loading machine. The picture was taken just prior to load initiation.

Figure 15:
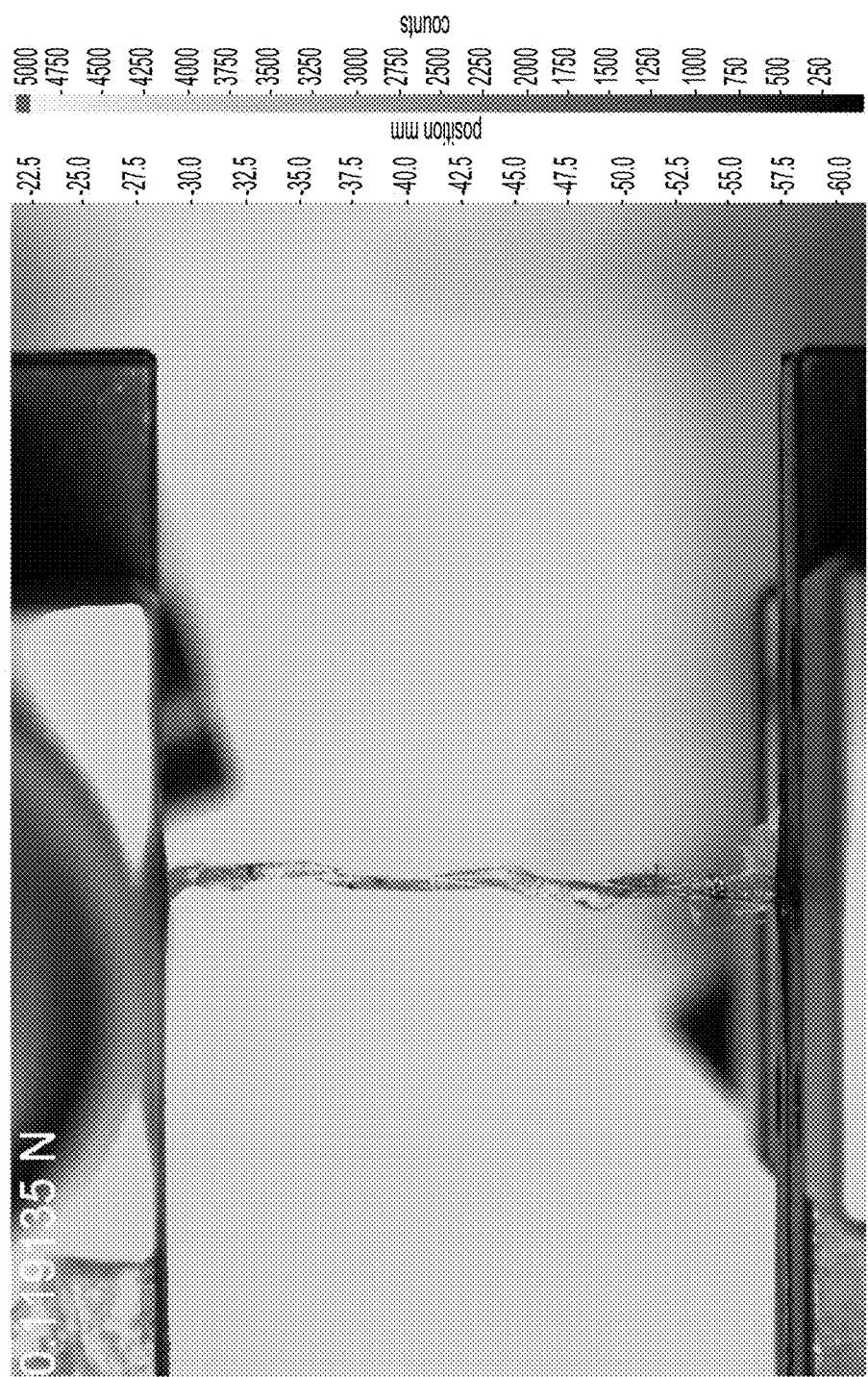

FIG. 15 is a photograph of soft coral long collagen fibers collected as braided bundles. These bundles were braided around an elastomeric band to form a long hybrid composite wire. The wire was placed in a uniaxial mechanical loading machine and subjected to a stretch to failure.

Figure 16A:
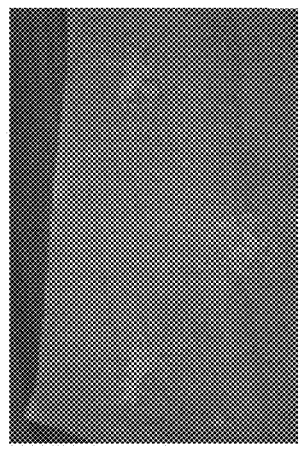

FIG. 16A is a photograph of three piles of chopped collagen fibers.

Figure 16B:
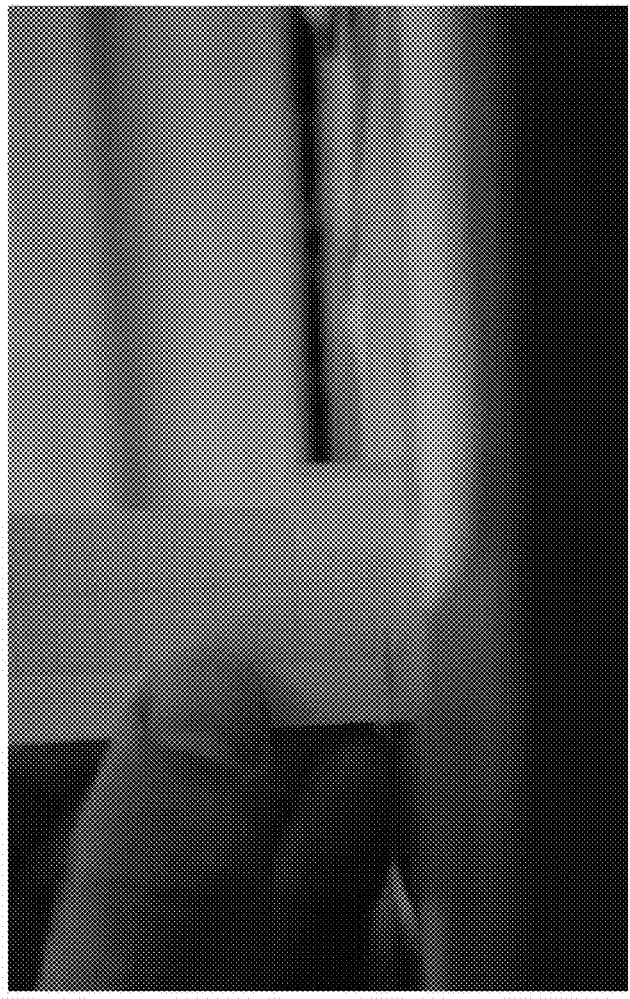

FIG. 16B is a photograph of a cylindrical sample of Agar hydrogel reinforced with chopped strands of soft coral collagen fibers forming a solidified composite media.

Figure 17:

FIG. 17 is a photograph of a top view of a cylindrical sample of Agar hydrogel reinforced with chopped strands of soft coral collagen fibers forming a solidified composite media.

Figure 18:
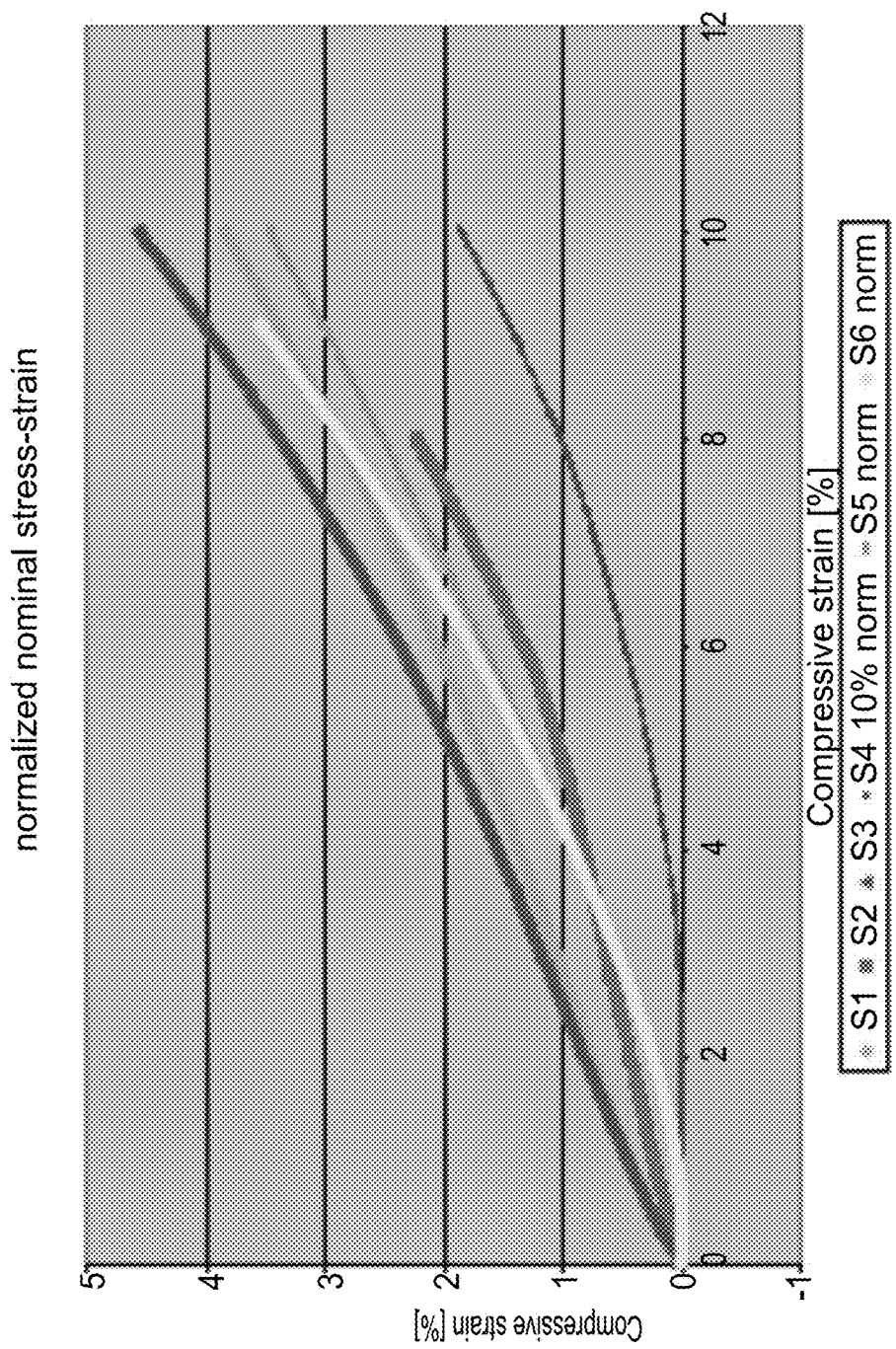

FIG. 18 is a graph of stress versus strain of a composite hydrogel reinforced with chopped strands of soft coral collagen fibers. Six samples were used in this test. The first three samples were reinforced with collagen fibers while the other control samples included matrix only media. Different mechanical loading rates were imposed on the three samples and their correspondent control. The figure shows the upper bond higher stiffness response of the composite samples (greenish colors) while the control matrix samples (bluish colors) exhibiting lower stiffness nonlinear behavior.

Figure 19:
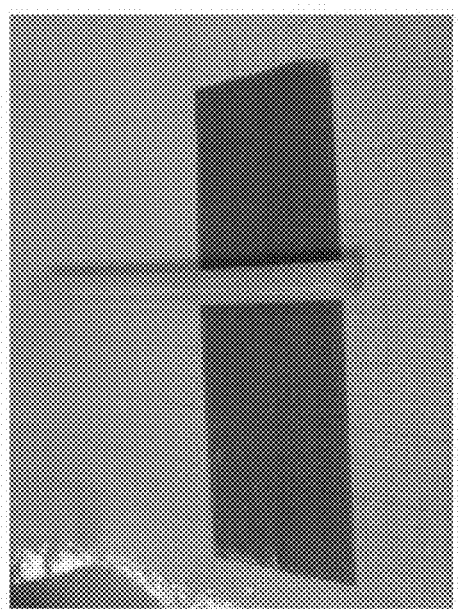

FIG. 19 is a photograph of a cylindrical shape matrix construct made without collagen fibers from alginate with cross-linking agent, EDC/NHS, to serve as a control sample.

Figure 20:
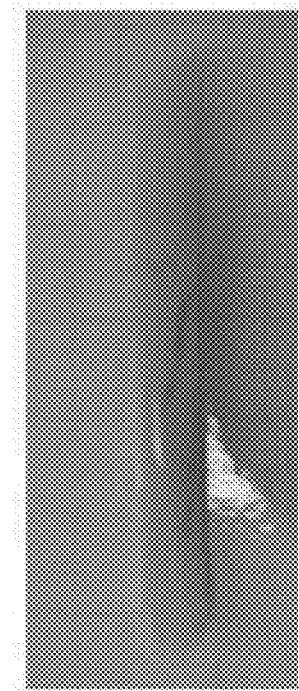

FIG. 20 is a photograph of a cylindrical shaped biocomposite with 7 collagen fiber bundles initially self cross linked and further cross-linked with the alginate hydrogel matrix.

Figure 21:
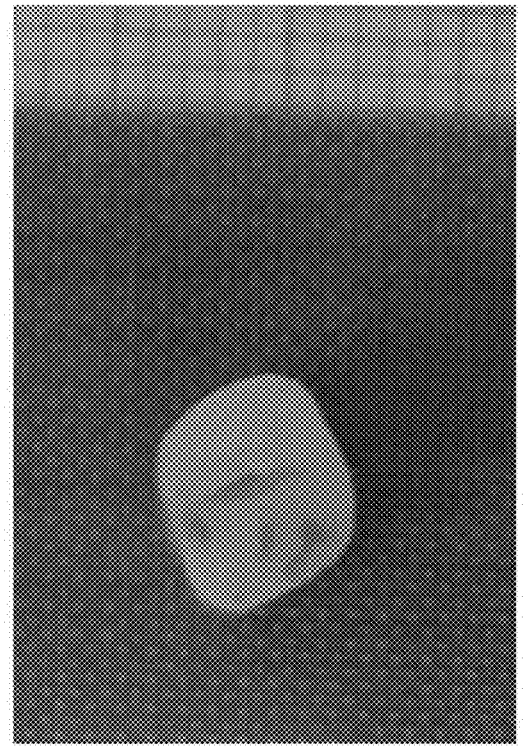

FIG. 21 is a photograph of a cross-section of the biocomposite cylindrical sample where it has been subjected to axial stretch. The cross section has initially failed in the non-reinforced area as shown on the right bright side.

Figure 22:
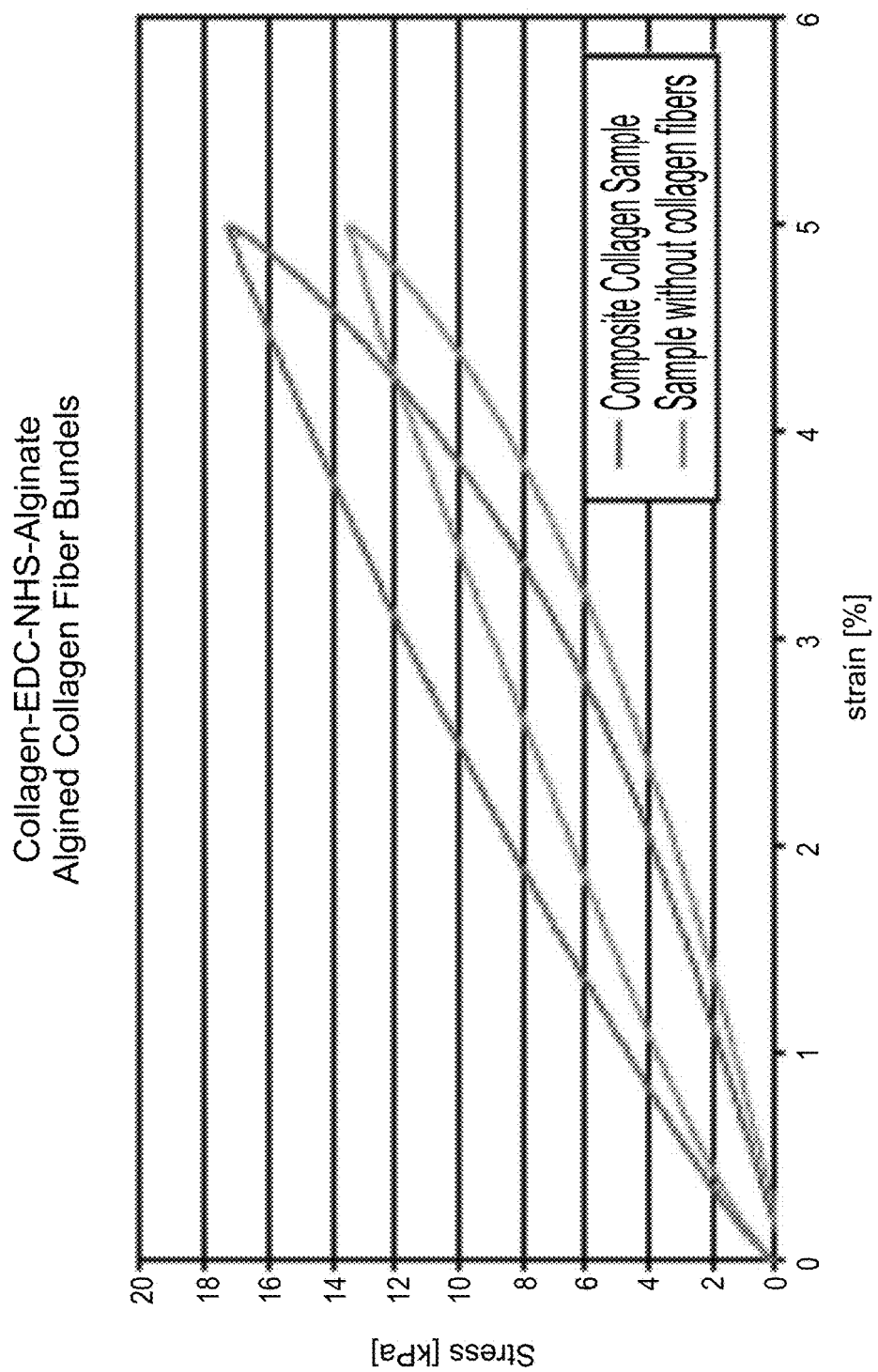

FIG. 22 is a graph illustrating stress versus strain of a bio-composite cross-linked collagen with alginate hydrogel along with the stress-strain response of the control sample without fibers clearly showing the added mechanical stiffness and increased energy (area under closed load cycle) as a result of the addition of the elastic collagen fibers. It should be noted that the same cross-linker used for the fibers was added in the control sample to account for a self matrix cross-linking effect.

Figure 23:

FIG. 23 is a photograph of a cylindrical alginate hydrogel matrix with crosslinked coral collagen fibers in Instron loading frame machine.

Figure 24:
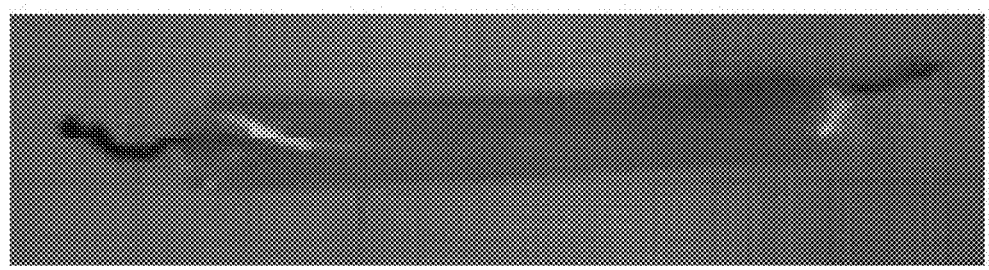

FIG. 24 is a photograph of a cylindrical shape biocomposite with a bundle of fibers in the axial orientation.

Figure 25:
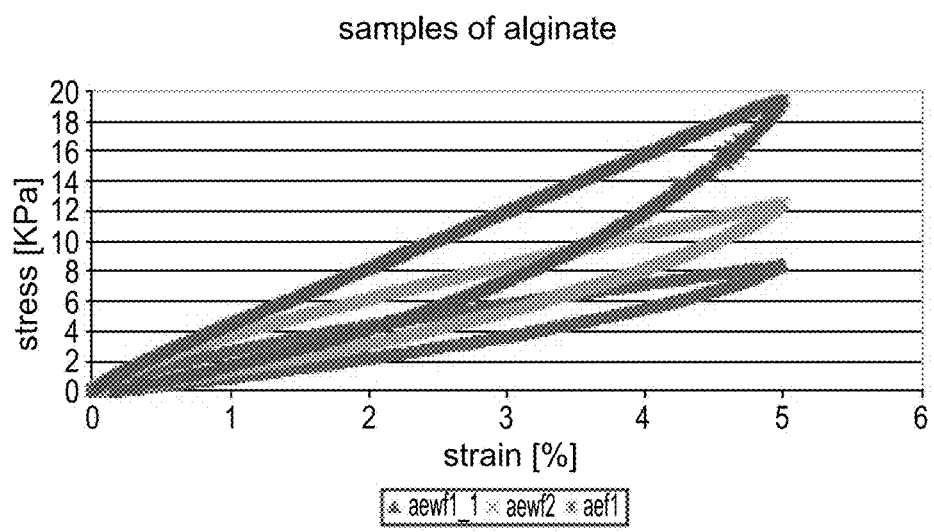

FIG. 25 is a graph illustrating the stress versus strain of a bio-composite comprising a cross-linked collagen with alginate hydrogel with a 7.7-13% fibers content. (aewf—alginate+edc+without fibers, aef—alginate edc+fiber). Fiber 1 was crosslinked with genipin; and Fiber 2 was crosslinked with EDC-NHS.

Figure 26:
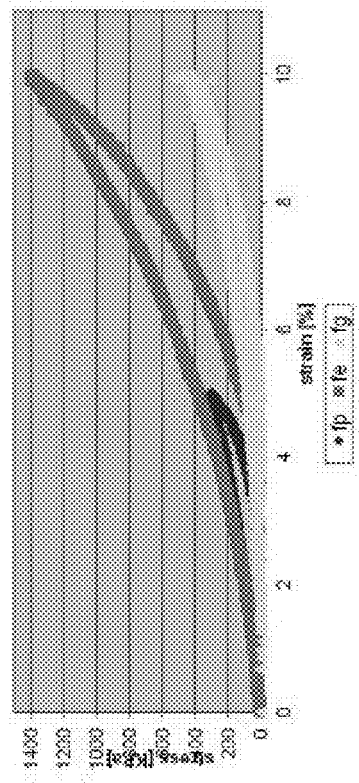

FIG. 26 is a graph illustrating stress vs. strain of crosslinked fibers. Fp: diameter 350 um, length: 60 mm, weight: 3 mg. Fe: fibers crosslinked with EDC/NHS (20 ul), diameter 400 um, length: 50 mm, weight: 3 mg, Fg: fibers crosslinked with genipin (60 ul, 1 mg/ml) diameter 350 um, length: 65 mm, weight: 3.5 mg.

Figure 27:
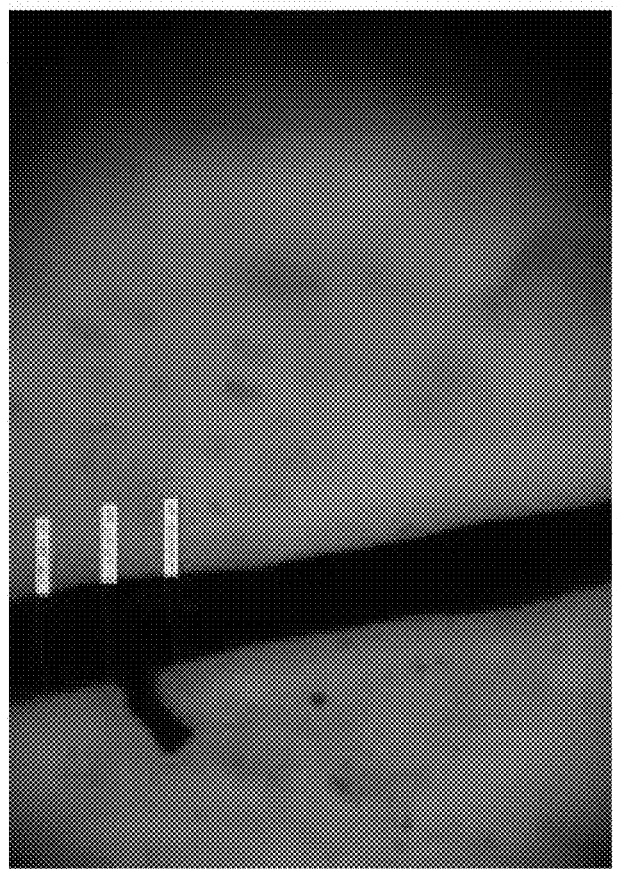

FIG. 27 is a light microscope image of pure collagen bundle (magnification ×5).

Figure 28:
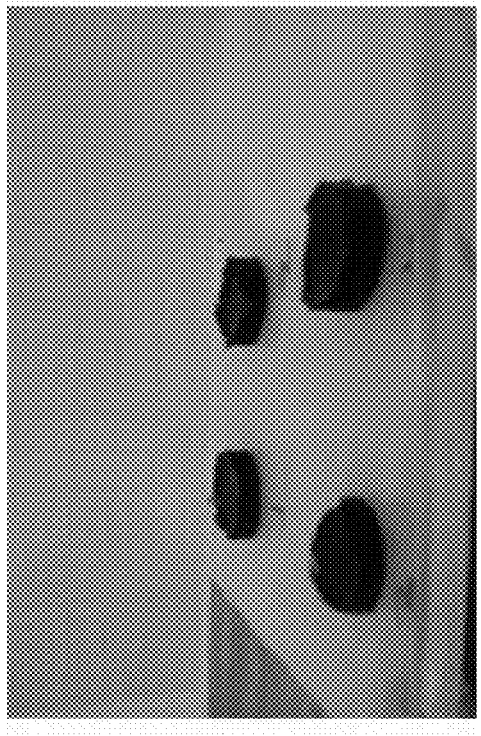

FIG. 28 are photographs of samples of chitosan matrix crosslinked with genipin with and without collagen fibers.

Figure 29:

FIG. 29 is a photograph of coral collagen fiber crosslinked to matrix of chitosan hydrogel using genipin crosslinker.

Figure 30:
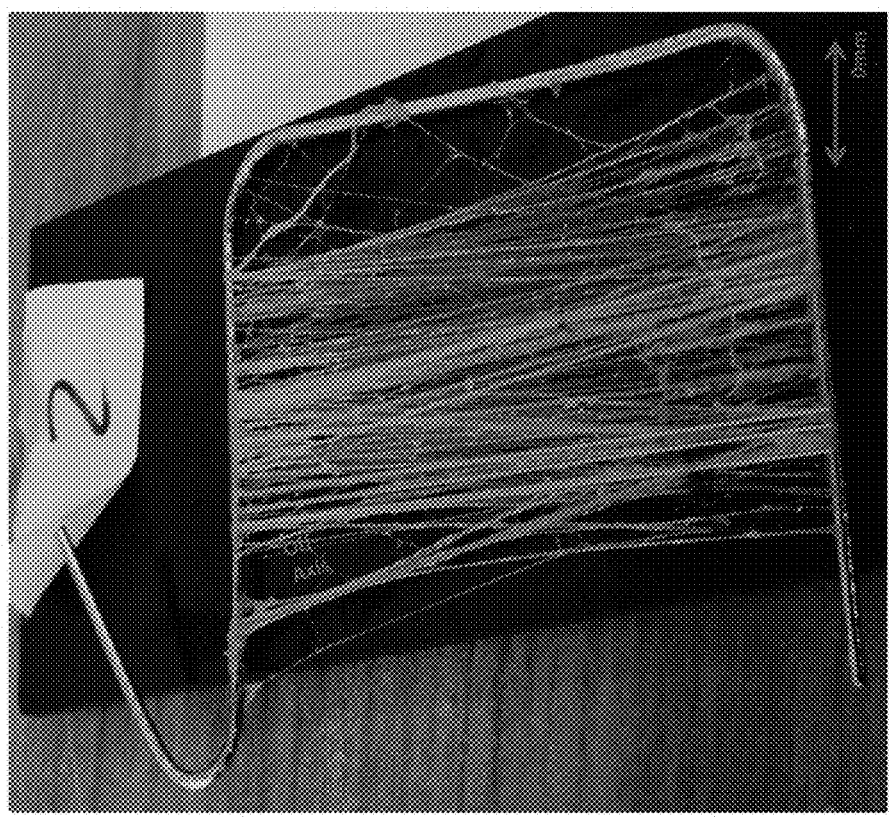

FIG. 30 is a photograph of coral collagen fibers on a U shaped wire. Fiber angles are controlled, e.g. the green-marked fibers are aligned in the tensile axis direction. The red-marked fibers are aligned in the off-axis direction.

FIGS. 31A-E are photographs and diagrams illustrating extraction of collagen fibers and fabrication thereof into a biocomposite material. A—Coral fiber extrusion. B—illustration of wrapped coral fibers on U shaped wire. C—fabrication of unidirectional oriented coral collagen fibers. D—Alginate matrix hydrogel gelation with crosslinking of collagen fibers. E—Final composite.

Figure 32:
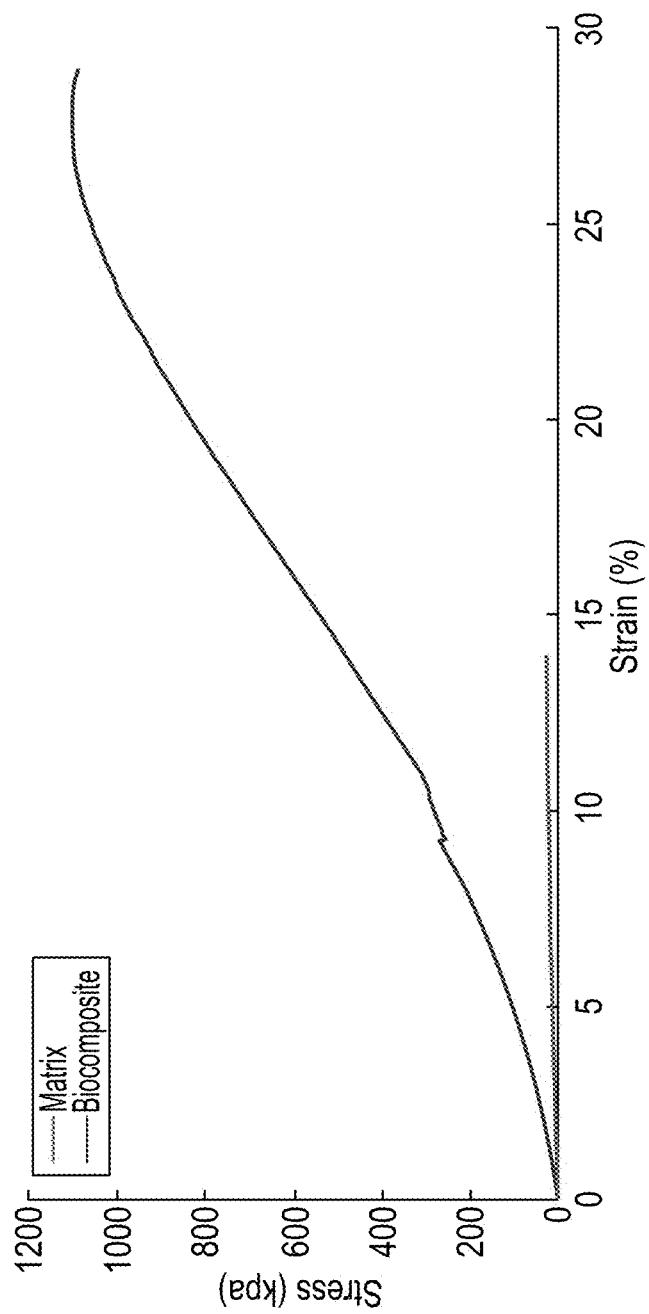

FIG. 32 is a stress-strain plot illustrating the mechanical monotonic behavior of the biocomposite vs. matrix (control).

Figure 33:
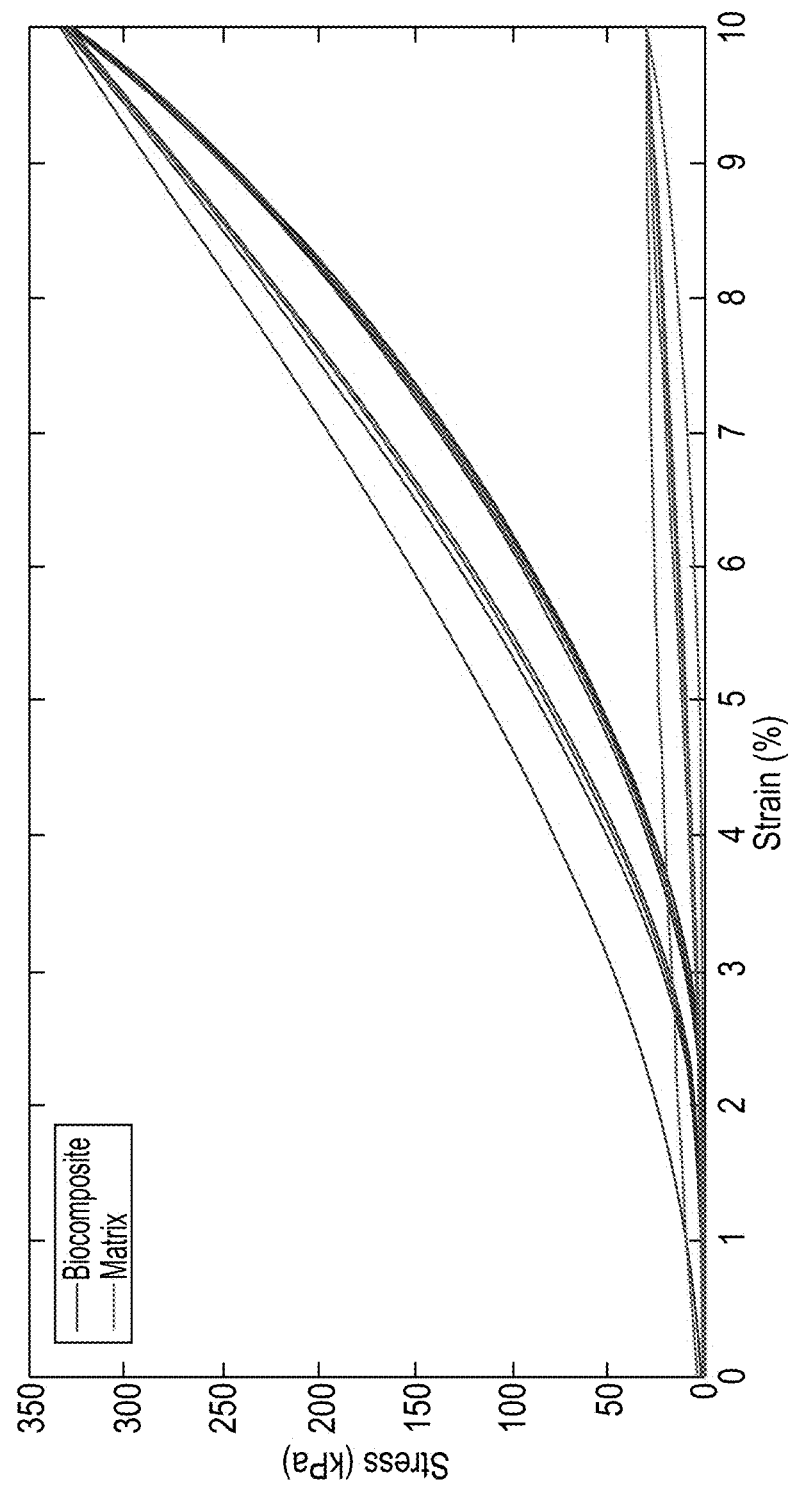

FIG. 33 is a stress-strain plot illustrating the mechanical cyclic behavior of the biocomposite vs. matrix (control) at 10% strain.

Figure 34C:
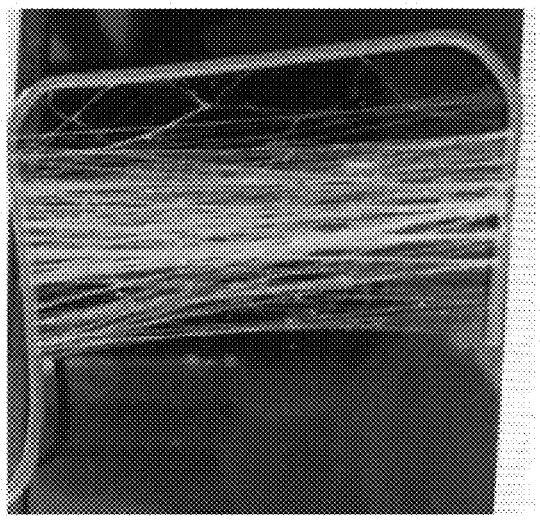
Figure 34B:
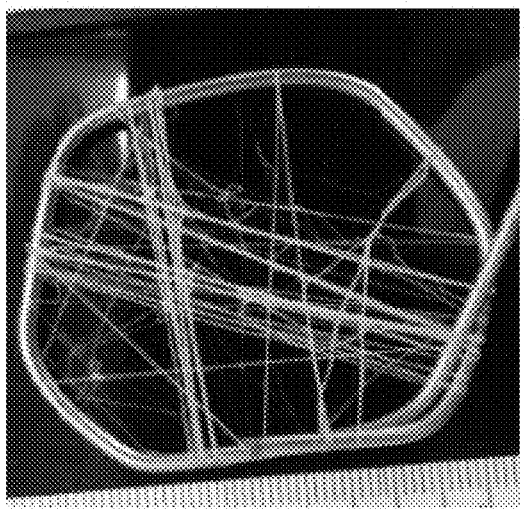
Figure 34A:
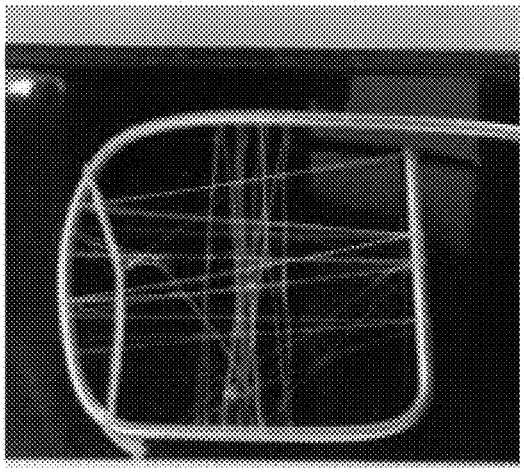

FIGS. 34A-C are photographs illustrating the design and organization of the collagen fibers before fabrication: (A) cross-ply 0/90° fibers, (B) angle-plied ±33° and (C) aligned unidirectional (0°) mounted on stainless steel wire frames.

Figure 35C:
Figure 35B:
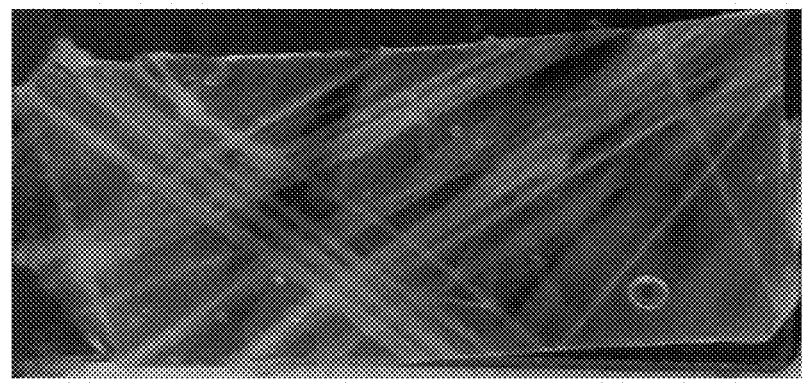
Figure 35A:
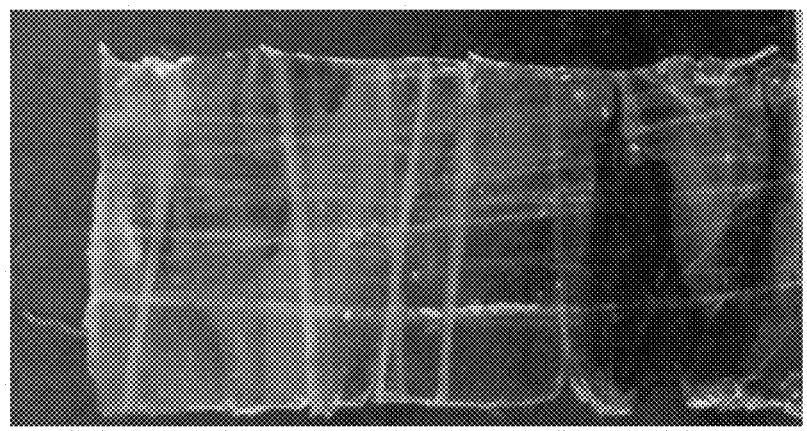

FIGS. 35A-C are photographs illustrating three biocomposites with basic orientations, (A) cross-ply (0/90°), (B) angle-ply (±33°) and (C) unidirectional (0°) cut as rectangular strips to be mechanically stretched.

Figure 36:
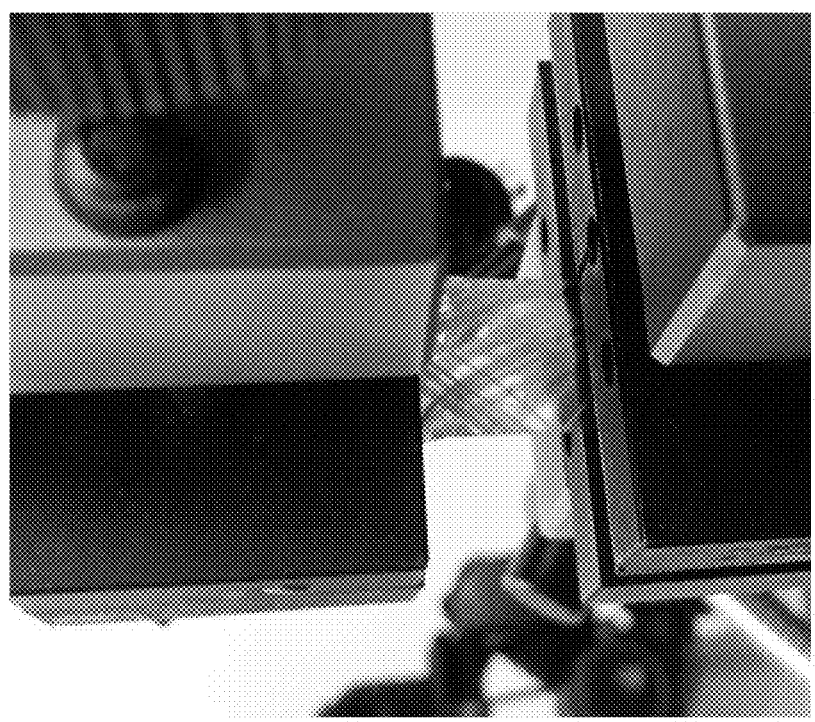

FIG. 36 is a photograph illustrating mechanical stretching of an angle-ply composite.

Figure 37:
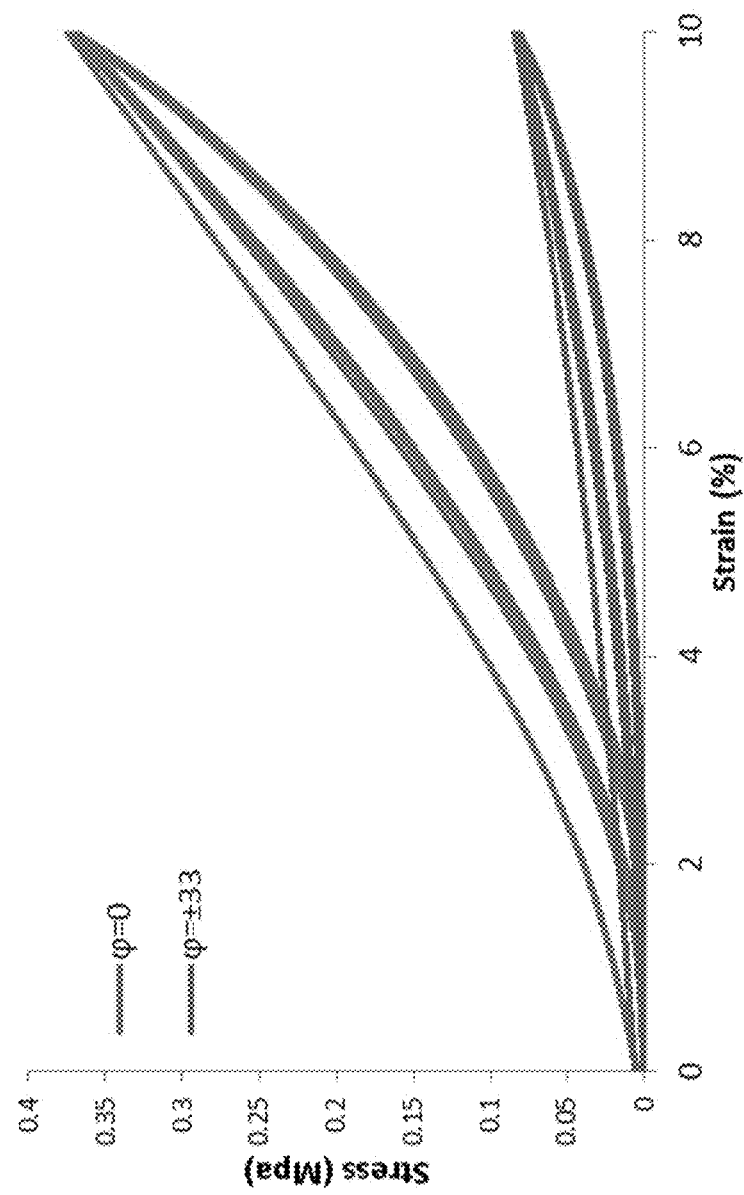

FIG. 37 is a stress strain plot of cyclic response for two bio-composite systems one having unidirectional fibers composite and the other bidirectional fibers composite.

Figure 38:
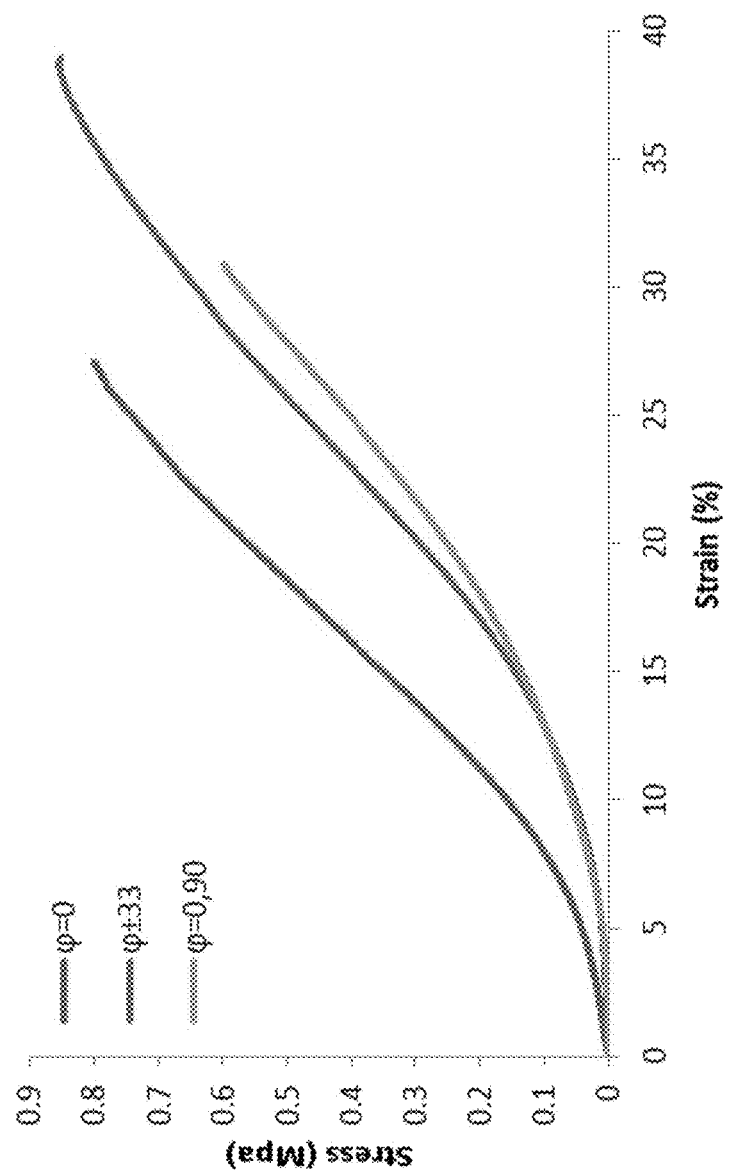

FIG. 38 is a graph illustrating the results of static stretch tests to failure of three biocomposites with different fiber orientations.

DESCRIPTION OF SPECIFIC EMBODIMENTS OF THE INVENTION

The present invention, in some embodiments thereof, relates to biological composites comprising collagen and, more particularly, but not exclusively, to collagen derived from *Sarcophyton* sp. coral.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Collagen is the principal structural protein in the body and constitutes approximately one-third of the total body protein. It comprises most of the organic matter of the skin, tendons, bones and teeth and occurs as fibrous inclusions in most other body structures. Some of the properties of collagen are its high tensile strength; its ion exchanging ability, due in part to the binding of electrolytes, metabolites and drugs; its low antigenicity, due to masking of potential antigenic determinants by the helical structure, and its low extensibility, semipermeability, and solubility. Furthermore collagen is a natural substance for cell adhesion. These properties make this protein suitable for fabrication of bioremodelable research products and medical devices such as implantable prostheses, cell growth substrates, and cellular and a-cellular tissue constructs.

The present inventors have identified collagen extracted from *Sarcophyton* sp. coral as a key component for the fabrication of novel composite biomaterials having superior mechanical properties for use in industrial and other medical applications such as orthopedic repair of osteoarthritic joints, damaged ligament, degenerated annulus and nucleus tissue of spine discs, and reconstruction of failed tendons, among many others. In addition, laminated composite collagen-films may be used to make patch-constructions for cardiovascular-repair of damaged leaflets and arteries and for repair of various soft tissues.

Whilst reducing the present invention to practice, the present inventors generated numerous collagen-based composites and showed that they possessed superior behavior (e.g. elasticity and or tensile strength) as compared with the composite material devoid of the collagen.

Specifically, the present inventors generated an agar hydrogel reinforced with *Sarcophyton* sp. coral, long collagen fiber bundles—FIGS. 1-4; porcine collagen hydrogel reinforced with *Sarcophyton* sp. coral, long collagen fiber bundles—FIGS. 5-7; polymeric resin reinforced with *Sarcophyton* sp. coral, collagen fibers and sodium alginate hydrogel reinforced with *Sarcophyton* sp. coral collagen fibers.

The present inventors propose that the *Sarcophyton* sp. coral collagen fibers of the proposed composites may be manipulated such that they are restricted to particular lengths (e.g. short, chopped fibers) or braided, knitted, tied or weaved so as to form bundles of longer fibers.

Thus, according to one aspect of the present invention there is provided an isolated composite comprising, as a first component, collagen fibers extracted from a *Sarcophyton* sp. coral and a second component selected from the group of biopolymers consisting of an alginate, agar, a non-coral collagen, a chitosan and a synthetic polymer.

As used herein the term "composite" refers to a substantially solid material that is composed of two or more discrete materials, each of which retains its identity, e.g., physical characteristics, while contributing desirable properties to the composite.

The composites can be in any form such as laminated layers, films, injectable fillers, twisted fibers or bundles.

The term "isolated" as used herein refers to the composite being substantially free from other substances (e.g., other cells, proteins, nucleic acids, etc.) in its in-vivo environment (i.e. in the coral itself).

The term "collagen" as used herein, refers to a polypeptide having a triple helix structure and containing a repeating Gly-X-Y triplet, where X and Y can be any amino acid but are frequently the imino acids proline and hydroxyproline. According to one embodiment, the collagen is a type I, II, III, V, XI, or biologically active fragments therefrom.

As used herein, the phrase "collagen fiber" refers to a non-soluble self-aggregate of the above-mentioned collagen comprising a fibrous structure in which collagen molecules are packed in series and also in parallel.

*Sarcophyton* coral may be retrieved directly from a reef in the sea (e.g the Red Sea) or may be farmed artificially.

Examples of *Sarchophyton* species in which the collagen fibers may be retrieved include for example, *Sarcophyton auritum, Sarcophyton ehrenbergi, Sarcophyton infundibuliforme, Sarcophyton pauciplicatum, Sarcophyton teniospiculatum* and *Sarcophyton trocheliophorum*.

In order to farm *Sarcophyton* sp. coral, it may be attached to a clay surface and grown under conditions which support propagation.

The coral may be attached to a clay surface using any method known in the art, including for example tethering (e.g. plastic ties, rubber bands, wire or thread, stitches, suspension; adhering (e.g. cyanoacrylate/super glue); capturing (e.g. cementing and epoxying); and impaling (e.g. drilling, pegging and spearing).

The coral may be attached to the clay surface immediately following retrieval from a reef or alternatively may be processed (e.g. by cutting) prior to attachment. According to one embodiment, the soft coral is cut up into pieces of less than about 50 mm$^2$ and greater than about 25 mm$^2$.

Exemplary conditions for propagating the soft coral comprise a water temperature at a range of about 20-26° C. under a light intensity range of about 35-130 µE.

According to one embodiment the pH of the water in which the soft coral is propagated is about 8.2.

According to one embodiment when the temperature is about 20° C., the light intensity is about 230 µE.

According to one embodiment when the temperature is about 26° C., the light intensity is about 250 µE.

According to this aspect of the present invention, a soft coral may be propagated for at least six months, at least one year or even longer. An increase of volume of the soft coral cuttings may be as much as 60 times following propagation after 8-12 months, according to the method of the present invention.

Extraction of collagen from the *Sarcophyton* sp. coral may be effected by manual extraction using an implement such as tweezers. A detailed description of *Sarcophyton* extraction is provided in Example 11.

Additional properties of the *Sarcophyton* sp. coral of the presently described composites are provided in WO2009/118734, incorporated herein by reference.

Following extraction, the collagen may be crosslinked so as to increase its stability or durability.

The term "cross-linked" as used herein refers to a composition containing intermolecular cross-links and optionally intramolecular cross-links arising from the formation of covalent bonds, ionic bonds, hydrogen bonding, or any combination thereof.

Crosslinking of collagen-based materials of the present invention may also be used to suppress the antigenicity of the material in order to prevent the hyperacute rejection reaction. In addition, crosslinking may used to improve mechanical properties and enhance resistance to both mechanical and proteolytic degradation.

Several chemical crosslinking methods for collagen-based materials are known—see for example U.S. Pat. Application Publication No. 20050136510. These methods typically involve the reaction of a bifunctional reagent (i.e., a spacer) with the amine groups of lysine or hydroxylysine residues on different polypeptide chains or the activation of carboxyl groups of glutamic and aspartic acid residues followed by the reaction with an amine group of another polypeptide chain to give an amide bond. For example, glutaraldehyde (GA), which is a bifunctional aldehyde, or diisocyanates bridge amine groups on two adjacent polypeptide chains to form crosslinks. Another method of crosslinking involves the formation of an acyl azide. The acyl azide method involves the activation of carboxyl groups in the polypeptide chain. The activated groups form crosslinks by reaction with collagen amine groups of another chain.

Also, water-soluble carbodiimides can be used to activate the free carboxyl groups of glutamic and aspartic acid moieties in collagen. Activation of the carboxyl groups with carbodiimides, such as 1-ethyl-3-(3-dimethylaminopropyl) carbodiimide.HCl (EDC), gives O-acylisourea groups. A condensation reaction by nucleophilic attack of a free amine group of a (hydroxy) lysine residue with urea as a leaving group results in formation of an amide crosslink. The O-acylisourea can also be hydrolyzed or rearranged to an N-acylurea, which is much more stable and will not react to form a crosslink. Addition of N-hydroxysuccinimide (NHS) prevents this rearrangement, however. In the presence of NHS, the O-acylisourea can be converted to an NHS activated carboxyl group, which also can react with a free amine group to form a crosslink.

Other methods of crosslinking may also be used to crosslink the collagen of the present invention such as by glycation using different sugars, by Fenton reaction using metal ions such as copper, by lysine oxidase and/or by UV radiation.

In embodiments, the collagen fibers may be utilized to generated composites without treatment or processing. In other embodiments, the fibers may be processed into wovens, braids, wires, nonwovens, fiber webs, meshes and/or felts. Fiber webs and similar structures may be formed by knitting, needling, interlooping, entangling, melting, or sealing of the fibers.

Where the fibrous polymeric component is in the form of a nonwoven, web, mesh or felt, the void volume of such a component may be above about 50% to, in embodiments above about 90% of the component.

In other embodiments, the fibers may be cut (e.g. chopped) such that the length of each fiber is between about 1 mm-50 mm, 1 mm-40 mm, 2 mm-40 mm, 2 mm 30 mm, 2 mm-20 mm, 2 mm-10 mm.

The present invention contemplates a myriad of agents together with the above disclosed collagen which may be used to fabricate the composites of the present invention.

According on one embodiment, the agent is a polymerizable agent.

The polymerizable agent of the present disclosure may include monomers, macromers, oligomers, polymers, or a mixture thereof. The polymerizable agent may include covalently crosslinkable polymers, ionically crosslinkable polymers, polymers crosslinkable by redox chemistry, polymers crosslinked by hydrogen bonding, or any combination thereof. In embodiments, the polymerizable agent may be substantially hydrophilic and biocompatible.

In embodiments the polymerizable agent may be in a solution. As used herein, a "solution" includes a solution, a suspension, and/or a colloid.

According to another embodiment, the polymerizable agent is a hydrogel forming agent.

The term "hydrogel" as used herein refers to a hydrophilic cross-linked polymer capable of containing a large volume fraction of water. In some embodiments, hydrogels according to the present disclosure can contain greater than about 70-90 volume % water. When a hydrophilic polymer is formed in situ, it may inherently acquire water from its environment or from solutions used to create the hydrogel.

The hydrogels can be a single block with a molecular weight of at least about 600, in embodiments about 2000 or more, in other embodiments at least about 3000. Alternatively, the hydrogels can include two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

Nonlimiting suitable materials which may be used to form hydrogels include synthetic polymers such as polyalkylene oxides including poly(ethylene glycol), poly(ethylene oxide), and poly(ethylene oxide)-co-poly(propylene oxide) block copolymers (poloxamers and meroxapols), partially or fully hydrolyzed polyvinyl alcohol), poly(vinylpyrrolidone), poly(ethyloxazoline), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as FICOLL™, polysucrose, hyaluronic acid, dextran, heparan sulfate, chondroitin sulfate, heparin, or alginate, and proteins such as gelatin, non-coral collagen, albumin, or ovalbumin or copolymers or combinations thereof.

As used herein, "celluloses" includes cellulose and derivatives of the types described above; "dextran" includes dextran and similar derivatives thereof.

Other materials which can be used as the polymerizable agent to form a hydrogel include alginates. Alginate is a carbohydrate polymer isolated from seaweed, which can be crosslinked to form a hydrogel by exposure to a divalent cation such as calcium as described, for example, in WO 94/25080, the entire disclosure of which is incorporated herein by this reference. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel and the alginate polymers may be derivatized with hydrophobic, water-labile chains, e.g., oligomers of epsilon-caprolactone. The hydrophobic interactions induce gelation, until they degrade in the body.

Additionally, polysaccharides which gel by exposure to monovalent cations, including bacterial polysaccharides such as gellan gum, and plant polysaccharides such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, may also be useful. For example, hyaluronic acid, which forms an injectable gel with a consistency like a hair gel, may be utilized. Modified hyaluronic acid derivatives may be particularly useful. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and derivatives thereof are available from Genzyme, Cambridge, Mass. and Fidia, Italy.

Other polymeric hydrogel precursors which may be utilized include polyethylene oxide-polypropylene glycol block copolymers such as PLURONICS™ or TETRONICS™, which are crosslinked by hydrogen bonding and/or by a temperature change, as described in Steinleitner et al., Obstetrics & Gynecology, vol. 77, pp. 48-52 (1991); and Steinleitner et al., Fertility and Sterility, vol. 57, pp. 305-308 (1992). Other materials which may be utilized include proteins such as fibrin, collagen and gelatin. Polymer mixtures may also be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) can be combined to form a gel over the course of time, e.g., as quickly as within a few seconds.

According to one embodiment, the polymerizable agent is a polysaccharide.

Exemplary polysaccharides contemplated for the composites of the present invention include, but are not limited to chitin, agar, cellulose, starch, dextran, glucan, chitosan, alginate and hyaluronic acid. Thus, for example, the agent may be an alginate an agar or a chitosan.

According to another embodiment, the polymerizable agent is a polypeptide.

Examples of polypeptides include, but are not limited to elastin, spider silk, silk-worm silk, non-coral collagen such as an animal derived collagen (e.g. porcine collagen), fibronectin, fibrin, fibrinogen, resilin and mussel byssus protein.

According to a specific embodiment, the polypeptide agent is animal derived collagen.

According to another embodiment, the agent is a metal such as platinum, titanium and stainless steel.

According to another embodiment, the agent is a synthetic polymer. Examples of synthetic polymers include, but are not limited to poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolid-es) (PLGA), polyanhydrides, and polyorthoesters.

According to yet another embodiment, the agent is a mineral. Examples of minerals that may be used to fabricate the composites of the present invention include, but are not limited to calcium, magnesium, boron, zinc, copper, manganese, iron, silicon, selenium, phosphorus and sulfur.

In order to generate composites, the individual components (collagen and additional component) are placed together such that they are in contact one with the other. Any method of contacting is contemplated by the present invention including for example, mixing, blending, stirring, placing, coating, impregnating.

Exemplary ratio of the collagen:additional agent in the suspension include: 100/0, 90/10, 80/20, 70/30, 60/40, 50/50, 40/60, 30/70, 20/80, 10/90, and 0/100.

It will be appreciated that as well as crosslinking the coral scaffold prior to generation of the composite, alternatively or additionally, a crosslinking step may be effected following generation of the composite to further enhance boding of the collagen with the second component.

The type of crosslinking typically depends on the second agent of the composite.

In order to enhance formation of the composite, the composite may be subjected to radiation. Suitable radiation treatments are within the purview of those skilled in the art and include, but are not limited to, ultraviolet (UV) radiation. The radiation treatment may enhance polymerization of the collagen with itself and/or the second component.

To increase the porosity of the composite (in order to generate a scaffold for tissue generation) or to enhance bonding of the components of the composite, the composite may be dried. According to a particular embodiment, the composite is frozen and freeze-dried.

Typical freeze-drying is achieved through the use of standard commercial freeze-drying equipment. In a particular embodiment, the freeze-drying of the collagen composite facilitates the formation of a porous structure throughout the internal structure of the composite. The pores formed through the internal structure of the scaffold may be of any reasonable size to facilitate cell attachment and new tissue formation when the scaffold is placed at the site of the implant. In a particular embodiment, the collagen after freeze drying can have pores about 0.01 mm to about 3.0 mm diameter in size.

According to one embodiment, during preparation of a hydrogel composite, the collagen fibers are inserted into or on top of the non-set gel (in an orientated or non-orientated fashion), such that when the gel is set, the collagen is bonded together with the hydrogel.

Alternatively, mixed solutions of collagen and hydrogel forming agents are generated which may be cast onto suitable molds (e.g. Teflon or polystyrene) following which appropriate assembly and crosslinking is optionally effected.

The present invention also contemplates coating the novel composites. According to one embodiment, the coating is comprised of the coral collagen described herein. In this method, following the crosslinking of the composites, dipping in solutions of the coral collagen may be carried out. The coral collagen in the coating will typically be absorbed into the composite. Following coating, a suitable polymerization method may be used.

The composites of the present invention may be combined with other polymers in blends and adducts to manipulate the degradation and mechanical properties of the material. Practically any biocompatible polymer may be combined with the composites. In a preferred embodiment, the added polymer is biodegradable. Exemplary biodegradable polymers include natural polymers and their synthetic analogs, including polysaccharides, proteoglycans, glycosaminoglycans, collagen-GAG, collagen, fibrin, and other extracellular matrix components, such as elastin, fibronectin, vitronectin, and laminin Hydrolytic ally degradable polymers known in the art include, for example, certain polyesters, polyanhydrides, polyorthoesters, polyphosphazenes, and polyphosphoesters. Biodegradable polymers known in the art include, for example, certain polyhydroxyacids, polypropylfumerates, polycaprolactones, polyhydroxyalkanoates, poly(amide-enamines), polyamides, poly (amino acids), polyacetals, polyethers, biodegradable polycyanoacrylates, biodegradable polyurethanes and polysaccharides. For example, specific biodegradable polymers that may be used in the present invention include but are not limited to, polylysine, poly (lactic acid) (PLA), poly (glycolic acid) (PGA), copolymers and mixtures of PLA and PGA, e.g., poly (lactide-co-glycolide) (PLG), poly (caprolactone) (PCL), poly (lactide-co-caprolactone) (PLC), and poly (glycolide-co-caprolactone) (PGC).

According to a particular embodiment, the polymer is a polymeric resin. The polymeric resin is not a polypeptide or a polysaccharide. Preferably, the polymeric resin is a synthetic polymer.

Those skilled in the art will recognize that this is an exemplary, not comprehensive, list of biodegradable polymers. The properties of these and other polymers and methods for preparing them are further described in the art. See, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. Nos. 4,806,621; 4,638,045 to Kohn; and U.S. Pat. No. 4,946,929 to d'Amore; see also Wang et al., J. Am. Chem. Soc. 123: 9480, 2001; Lim et al., J. Am. Chem. Soc. 123: 2460, 2001; Langer, Acc. Chen7. Res. 33: 94, 2000; Langer, J. Control Release 62: 7, 1999; and Uhrich et al., Chem. Rev. 99: 3181, 1999.

The composites of the present invention may also be combined with non-biodegradable polymers. For example, polypyrrole, polyanilines, polythiophene, and derivatives thereof are useful electrically conductive polymers that can provide additional stimulation to seeded cells or neighboring tissue. Exemplary non-biodegradable polymers include, but are not limited to, polystyrene, polyesters, non-biodegradable polyurethanes, polyureas, poly(ethylene vinyl acetate), polypropylene, polymethacrylate, polyethylene, polycarbonates, and poly(ethylene oxide).

In embodiments, it may be desirable to include a therapeutic agent in the composites described herein. Such therapeutic agents may include, for example, growth factors proteins, polysaccharides, nucleic acid molecules, and synthetic organic or inorganic molecules including drugs which may be useful for therapeutic, prophylactic, diagnostic purposes, or medicinal. Drugs which may be utilized include antibiotics, antivirals, chemotherapeutic agents, anti-angiogenic agents, hormones, drugs having an effect on vascular flow, anti-inflammatories, and many others routinely used.

The importance of biopolymer based biomaterials is constantly increasing in the field of reconstructive medicine. In the recent years, the focus of this field has turned from the search for inert materials for implantation to development of biopolymer based materials that interact with the tissue and promote its correct regeneration. Furthermore, synthetic implants often fail the test of long term biocompatibility requiring their replacement during the lifetime of a patient which is a major drawback. With respect to reconstructive medicine, polysaccharides and protein polymers have been extensively investigated.

When used in vivo, and in particular inside the body of a subject, e.g., a human patient, it is important that the composites of the present invention be biocompatible. A "biocompatible" material is not substantially mutagenic, antigenic, inflammatory, pyrogenic, or hemolytic. Furthermore, it must neither exhibit substantial cytotoxicity, acute systemic toxicity, or intracutaneous toxicity, nor significantly decrease clotting time. In vivo and in vitro tests for these undesirable biological activities are well known in the art; examples of such assays are given, for example, in U.S. Pat. No. 5,527,610, the contents of which are incorporated by reference. Also, when used in vivo, the materials may be biogradable.

In the event that toxicity or immunogenicity, for example, occurs in a relevant composite, methods for modulating these undesirable effects are known in the art. For example, "tanning" of the composite by treating it with chemicals such as aldehydes (e.g., glutaraldehyde) or metaperiodate will substantially decrease both toxicity and immunogenicity. Preferably, the composites used to make devices for in vivo use are also sterilizable.

As mentioned, the composites of the present invention may be used in the field of reconstructive medicine such as for the generation of scaffolds.

The present inventors contemplate use of the composites for a wide spectrum of medical applications, such as orthopedic repair of osteoarthritic joints, damaged ligament, degenerated annulus and nucleus tissue of spine discs, and reconstruction of failed tendons, among many others. In addition, laminated composite collagen-films may be used to make patch-constructions for cardiovascular-repair of damaged leaflets and arteries and for repair of various soft tissues.

It will be appreciated that the composite of the present invention may also be generated in vivo at the site of implant.

Thus, for example, the present invention further contemplates addition of the collagen and a polymerizable agent separately at the implant site, allowing in situ crosslinking. The composite and the polymerizable agent may be applied simultaneously or in any order. For example, the polymerizable agent may be applied to a tissue defect followed by the application of the composite, and then crosslinked in situ. In embodiments, the fibrous polymeric component may be applied to a tissue defect followed by the application of the polymerizable agent, and then crosslinked in situ. In other embodiments, the polymerizable agent may be applied to a tissue defect followed by the application of collagen component, followed by the application of additional polymerizable agent, and then crosslinked in situ. Any combinations of polymerizable agent and collagen component may be utilized to correct a tissue defect; multiple applications of the polymerizable agent and fibrous polymeric component may occur, in embodiments forming multiple layers, which may then be allowed to crosslink in situ to correct a tissue defect.

The composites of the present invention (or individual components thereof) may be introduced to the site of a tissue defect arthroscopically, or by similar means, including by catheter, laparoscope, thoracoscope, and the like, further minimizing trauma to the patient.

One could also apply an external mold to shape the composite. Additionally, by controlling the rate of polymerization, it may be possible to mold the biocompatible composite of the present disclosure similar to how one would mold clay.

In embodiments, the composite may be introduced into an area wherever a bulking agent is desired, i.e., a soft tissue deformity such as that seen with areas of muscle atrophy due to congenital or acquired diseases, or secondary to trauma, burns, and the like. An example of this would be the introduction of the composite in the upper torso of a patient with muscular atrophy secondary to nerve damage.

The composite can also be introduced as a bulking agent for hard tissue defects, such as bone or cartilage defects, either congenital or acquired disease states, or secondary to trauma or burns. An example of this would be the introduction of the composite into the area surrounding the skull where a bony deformity exists secondary to trauma.

The composite, or components thereof could also be introduced to a site of a tissue defect through a catheter having a sufficiently large exit opening, optionally with fluoroscopic, sonographic, computed tomography, magnetic resonance imaging, or other type of radiologic guidance. This would allow for placement of the composite to specific organs or other tissue regions in the body, wherever a bulking agent would be required.

Further, the composite, or components thereof could be introduced through a laparoscope or thoracoscope having a sufficiently large exit opening, to any intraperitoneal or extraperitoneal or thoracic organ. For example, the composite could be introduced in the region of the gastroesophageal junction for the correcting of gastroesophageal reflux. This could be performed either with a thoracoscope introducing the substance in the esophageal portion of the gastroesophageal region, or via a laparoscope by injecting the substance in the gastric portion of the gastroesophageal region, or by a combined approach.

The composite can also be applied during the course of reconstructive surgery, as well as anywhere in the human body where a biocompatible material is necessary. The composite, or components thereof can be introduced endoscopically, for example through a laryngoscope, for injection into the vocal chords for the treatment of dysphonia, or through a hysteroscope for injection into the fallopian tubes as a method of rendering the patient infertile, or through a proctoscope, for injection of the substance in the perirectal sphincter area, thereby increasing the resistance in the sphincter area and rendering the patient continent of stool.

Tears in fibrocartilage and soft tissue, especially meniscal tears including peripheral meniscal tears, may be repaired by application of compositions in accordance with the present disclosure to the site of the tear and thereby covalently binding the composite to the fibrocartilage or soft tissue. Typically, a tear in the vascular region of the meniscus is repaired using arthroscopic techniques. An instrument for application of the present compositions may be inserted through small incisions which serve as anterior knee portals. Sutures or clips may be passed through a meniscal repair instrument and through the meniscus as a supplemental support to maintain the torn edges in an approximated position. The use of the present compositions that include a polymerizable agent reapproximates the torn edges of the meniscus and allows for healing of the tear.

In another embodiment, the present compositions may be used to repair tears or defects in periosteum. Such defects in the periosteum frequently occur around bone fracture sites where it is usually destroyed and cannot serve as a membrane barrier against the dislocation of bone fragments. By application of compositions in accordance with the present disclosure to the site of the tear or defect, and thereby covalently binding the polymerizable agent to the periosteum, repair and/or regrowth of the periosteum can be achieved. Morphogenic proteins may also be combined with the fibrous polymeric component, the polymerizable agent, or both, which attract mesenchymal stem cells from the periosteum. The attracted elements are then directed to differentiate into bone forming cells, which are essential for new bone formation by the patient. Thus, by repairing the periosteum, the present compositions and methods may also assist in the regeneration of defects in bone.

In another embodiment, the present compositions may be used to attach periosteum and other extracellular matrices to cartilage, as part of a cartilage repair method. Cartilage defects frequently occur within diarthrodial joints, and a prior method used to attempt to repair these includes the implantation of cells into the defect site, and attachment of periosteum or other extracellular matrices over the defect site, by suturing in place. The suturing method is difficult and can damage the surrounding articular cartilage. By application of compositions in accordance with the present disclosure, wherein the polymerizable agent combines with the collagen and covalently attaches to the periosteum and cartilage, a repair of the articular cartilage may be achieved by formation of the biocompatible composite in situ.

In another embodiment, the present compositions may be used to attach preparations of subintestinal submucosa and other extracellular matrices to a tendon or ligament, as used to enhance repair of these tissues. Tendon and ligament tears frequently occur, for example in the rotator cuff of the shoulder, and surgical repair is used suturing the rotator cuff together and to the bone, with the inclusion of a subintestinal submucosa or other extracellular matrix preparations over the repair site, to enhance the repair. However, prior methods suture these materials in place, providing poor physical attachment over much of the repair area. By application of compositions in accordance with the present disclosure thereby forming a biocompatible composite in situ and adhering same to the rotator cuff, and optionally covalently attaching the polymerizable agent to any subintestinal submucosa or other extracellular matrix preparations which may also be used in repairing the defect, an improved repair may be achieved.

In some embodiments, the biocompatible composites of the present disclosure may be designed to possess compressive and tensile properties within the range of native articular cartilage and thus may be utilized to form a functional repair of a chondral defect, which may involve binding the biocompatible composite constructs of the present disclosure to articular cartilage surrounding the chondral defect. Moreover, covalent bonds between the polymerizable agent and host cartilage can be established, thus adhesion of the biocompatible composite to host cartilage can be achieved with tensile strength in the range of normal articular cartilage, without compromising cell viability. The biocompatible composite of the present disclosure may also be used for femoral chondyle repair.

The composite of the present disclosure may also be used to attach cartilage to bone, bone to bone, and in the repair of bone defects. Other tissues which may be repaired with a composite of the present disclosure include, but are not limited to, ligaments, tendons, skin, muscle, fascia, breast tissue, and the like. The composite of the present disclosure exhibits resiliency to repeat and extensive loading.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology"

Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Agar Matrix Samples:

All specimens were made from the same production batch of hydrogel. All collagen fibers were used from the same soft-coral specimen after it was deep-frozen for an extended period of time and were kept in 70% alcohol solution until use.

Composite samples were made from Agar matrix and long Collagen fibers for reinforcement. Agar matrix was made by dissolving 0.6 g of AGAR NOBLE and 0.36 g of NaCl within 40 cc of boiling water. The solution was cooled to 40° C. and then it was poured into circular edge-rectangular shape like mold of dimensions of about 5 mm width and 30 mm in height. FIG. 5 is a photograph of the mold that was use for all samples that were tested under tension. Each mold was filled with 0.87 cc Agar solution.

The reinforced samples, for compression and compression tests, were created by placing the collagen fibers in the mold randomly before the agar was purged. The solution was poured into the pre-designed cylindrical molds in order to create reinforced and unreinforced specimens. All samples were kept in refrigerator for 72 hours before they were examined.

Cable Samples:

Long fibers of collagen were removed from the 70% alcohol solution and allowed to remain in the open air to dry for an hour. Two samples were created, one only from collagen fibers and one from fibers tied with a rubber band. The fibers of the sample were glued together at one end. Then, the fibers were braided to form a cable and glued at the other end.

Testing Protocols:

All mechanical tests were executed using an Instron universal loading frame, model 5582 with a 100 N load cell. Optical digital image correlation (DIC) technique was employed, for deformation and stretch measurements, using the Lavision 2D StrainMaster system. The latter included a 12-bit CCD digital camera, analog to digital converter, for load data synchronization between the Instron machine, and its DaVis 7.4 software. Hydrogel samples were carefully removed from their molds, and sequentially tested under tension or compression by the loading machine under displacement control.

The test was recorded using the DIC system at a rate of 10 Hz. Carbon particles were scattered on the surface of the composite samples to provide a good contrast for the DIC acquisition.

Example 1

Agar Hydrogel Reinforced with Long Collagen Fiber Bundles

Results

Composite materials from agar matrix and long collagen fibers were made in an elliptic shape-like mold having several elliptical shaped slots as shown in FIG. 5. Collagen fibers were prepared as described in the materials and methods. In the first three slots, long fibers were placed prior to pouring of the agar hydrogel. Slots 4-6 include agar control samples without collagen fibers.

In addition, collagen composites were made from long collagen fibers in a matrix of commercial "super glue".

Figure 1:
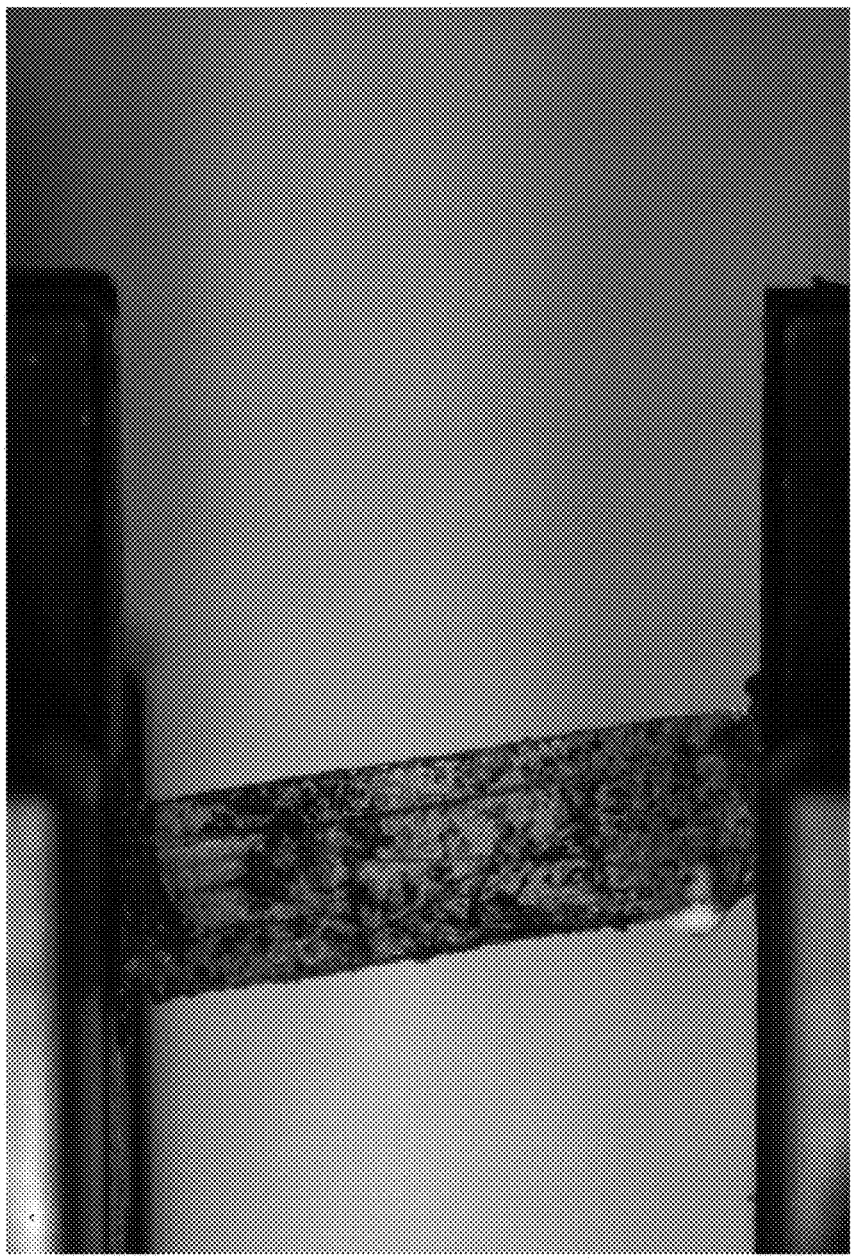

The intact film is illustrated in FIG. 1 whereby it was inserted in an axial mechanical loading frame. FIG. 1 shows the film after it was clamped at both ends and prior to subjecting it to axial loads. Limited collagen fiber bundles were embedded within the hydrogel and no special effort was made to ensure that all the fibers were aligned to the same degree. The composite media was able to maintain its rectangular shape despite the pressure applied at the ends from the clamping action and the fibers remained bonded with the matrix (hydrogel) media.

Figure 2:

FIG. 2 illustrates the collagen-fiber reinforced hydrogel film under tensile loading where failure was propagated from the lower clamp. The fibers continued to bear load and showed elastic behavior after this failure.

Figure 3:
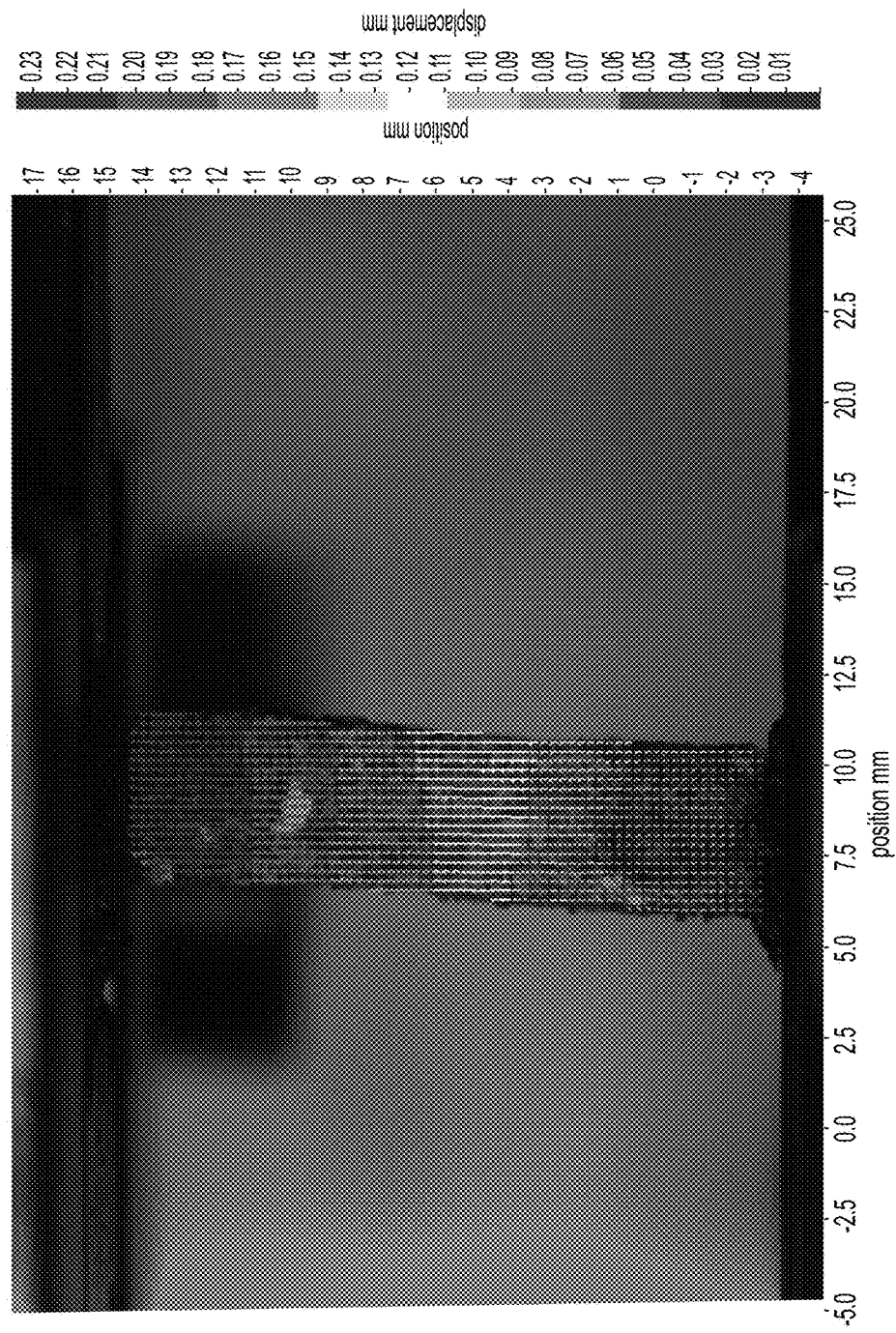

FIG. 3 shows Digital Image Correlation (DIC) results for agar hydrogel reinforced with long soft coral collagen fibers subjected to axial tension. The DIC method uses the optical images acquired during the test and a special software is used to process the displacement of the material on the surface of the film. The result in the form of an axial displacement field illustrates a linear field in this solidified film under tension. This indicates that both the fibers and matrix continued to mechanically bond at this stage of loading.

Figure 4:
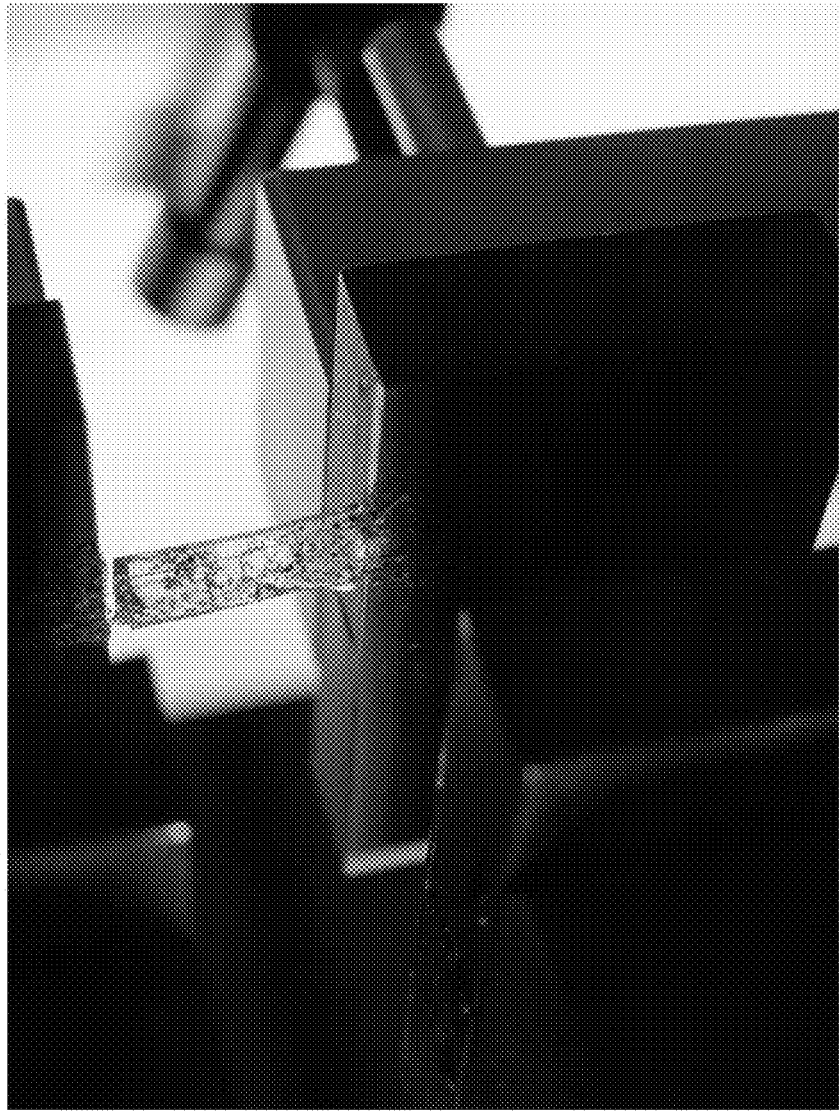

FIG. 4 illustrates a photograph taken after a tensile test where the film has completely failed at the ends of the clamps. However, the fibers continued to bear additional load at this stage.

Example 2

Collagen Matrix Reinforced with Long Collagen Fiber Bundles

The next composite material was constructed with soft-coral long collagen fiber reinforcing another second collagen matrix from animal (porcine) source. FIG. 5 displays the mold used to construct different collagen composite samples and shape their geometry. Six samples were made with the same geometry. The first three samples (1-3) are composite materials made from the soft coral collagen fiber bundles (macro-scale) with a collagen (micro-scale short fibers)

matrix binder. The other three (4-6) samples are the collagen matrix alone without reinforcement, used as controls.

FIGS. 6 and 7 are photographs of one of the composite samples. It shows the reinforced material under dehydrating conditions.

The samples comprise a mechanical bond between the two different collagen materials that form the composite due to the freeze-drying process.

Example 3

Collagen Matrix Reinforced by Cross-Linking with Long Collagen Fiber Bundles For this composite, collagen fibers and collagen matrix (as in Example 2) were chemically cross-linked to increase the mechanical bonding between them. FIG. 8 shows two collagen strips of materials with and without reinforcement in the form of long soft-coral collagen fibers. FIG. 9 illustrates mechanical loading of one of the strips. FIG. 10 shows the mechanical performance of the two strips in the form of load-strain curves for five consecutively repeated cycles. The reinforced composite sample clearly showed more hyperelastic behavior compared to the sample without reinforcement.

Example 4

Polymeric Matrix Reinforced with Long Collagen Fiber Bundles

The next composite material was constructed with soft-coral long collagen fiber reinforcing a synthetic polymeric material (plastic), polymeric resin. The goal of creating this composite was to demonstrate the ability to use the soft-coral long composite as reinforcement to an existing material that is currently used alone in the biomedical field and is approved for insertion in the human body. The lamination of these composite films is possible and the orientation of the fibers can be changed from lamina (composite membrane) to another. Another purpose of this feasibility manufacturing was to prove that it is possible to embed within and/or coat the polymeric material with long collagen fibers on its surface. The second option can be used to interface and contact the native tissue with the long collagen fibers to enhance bonding and tissue growth with the new composite construct. FIG. 11 illustrates a composite lamina (layer) reinforced with the long collagen fibers. The second sample (right) is the polymeric sample without reinforcement constructed for control testing. The dark texture seen on the sample is black and white spray paint that sprayed on the surface of these constructs for optical monitoring purposes when these samples are subjected to mechanical loading and continuously photographed.

Example 5

Long Collagen Fiber Bundles as Twisted Natural Wires

The following example describes formation of twisted fibers from collagen extracted from soft coral. The individual fibers were twisted upon extraction from the soft coral samples to form a wire with a cross-section having multi-fibers. FIG. 12 shows long collagen fiber bundles constructed with different numbers of fibers to form 4 different collagen bundled wires. These four wires were glued at their ends to a metallic specimen, mechanically stretched and the load elongation was measured to examine their elastic behavior compared to the single fiber.

FIG. 13 plots the load versus elongation curves for the combined four soft coral collagen long fiber bundles. The initial length of the wires (fiber bundles) was 10 mm. The mechanical loading included repeated cycles of uniaxial stretch up to 20% of initial length. All four fiber bundles withstood this level of stretch as evident by the similar loading curves showing the same elastic response. Each subsequent loading cycle shows a shifted response or initial displacement with zero loading (0.16 N) and then an increased stiffness and load resisting ability. This shift indicates a slip in the glued bundles and initial difference in their original height. Once all the curves were axially translated they indicate similar repeated elastic response. This behavior was previously found for the single fiber. Therefore, the effective mechanical behavior of the bundles show similar elastic properties and the flexibility of the combined fibers was preserved.

Example 6

Composite Cables-Wires Made from Long Collagen Fibers

Following removal of alcohol, collagen fibers were dried in the open air and then were assembled to form two types of cables. In the first type, long collagen fibers were tied with a rubber band. Three long collagen bundles and a thin rubber strip were glued together at their adages with commercial "super glue". After the glue dried a braid was braided and the second edge was glued together. In the second type, long collagen fibers were joined together as described herein above, but without the rubber band. After cable preparation, the samples were placed in 70% alcohol for 72 hours.

Individual fiber bundles were also made and stretched as shown in FIG. 14M. The wire was placed in a uniaxial mechanical loading machine. The picture was taken just prior to load initiation. Finally, FIG. 15 shows soft coral long collagen fiber bundles that were braided around an elastomeric band to form a long hybrid composite wire. The wire was placed in a uniaxial mechanical loading machine and subjected to a stretch to failure. It may be concluded that non-cross-linked long collagen fibers are possible in form of cables. The fibers are the major load carrier in cable type one.

Example 7

Randomly Chopped Long Collagen Fibers in Hydrogel Paste

Materials and Methods

Collagen was extracted as described herein above. Following drying, the collagen fibers were chopped to an average length of 2-3 mm (see FIG. 16A). Six samples were prepared using cylindrically shaped molds, 10 mm in diameter. Samples 1-3 included chopped fibers. Samples 4-6 were used as control without fibers. The agar hydrogel was made by dissolving 1.5% Agar and 0.9% salt in 40 ml of boil tap water.

The agar hydrogel was poured into the mold following cooling to 40° C. All samples were stored at 4° C. for 72 hours prior to compression testing using Instron tension and compression machine. Each of the samples was loaded to 10% of strain. Preconditioning five compression cycles were applied to the samples, whereas the sixth cycle was considered as measurement.

Results

The next soft collagen fiber composite material was made by chopping the long fibers into relatively small fibers (whiskers) mixed with a hydrogel matrix binder. The composite can be in the form of an injectable paste or solidified and molded into a small cylindrical shape as shown in FIGS. 16B and 17. Samples with and without collagen fiber reinforcement were made and tested under mechanical compression to compare the effect of adding different volumes of chopped long collagen fibers. FIG. 18 shows the compression stress-strain curves of the two samples (with and without added fibers) under different loading rates. It can be seen that for all rates the composite samples with added fibers showed an increase in stiffness and strength yet kept the elastic deformation behavior without any mechanical failure up to 10% of compressive strain. This indicates a repeated and large elastic behavior similar to native soft tissue materials.

Example 8

Long Collagen Fibers Cross-Linked with Sodium Alginate Hydrogel: Collagen-EDC-NHS-Alginate Materials and Methods:

Sodium Alginate 5% w/v 2.5 gr/50 ml was diluted in DDW pH 7 (Sigma Aldrich, W201502).

$CaCl_2 2H_2O$ (Acros, 207780010) 0.1M in DDW.

Dialysis tube membrane CelluSep T2 MWCO 6000-8000 Da (0.32 ml/cm) [8015-10]-6.37 mm dry diameter.

EDC-1-Ethyl-[3-dimethylaminopropyl]carbodiimide-75 mg/ml (Danyel biotech).

NHS-N-hydroxysuccinimide—115 mg/ml (Danyel biotech).

Sarcosiv-colony 11-coral collagen fibers.

Alginate+EDC/NHS (Control Samples):

About 15 cm of dialysis membrane was washed in DDW. One side of the membrane was tied. 10 µl of EDC+10 µl of NHS were mixed in an eppendorff tube. The EDC/NHS solution and 3 ml of 5% w/v Sodium alginate were inserted to the membrane tube and mixed mechanically. An additional tie was performed on the open side. The full tube was inserted into a 15 ml tube filled with $CaCl_2 2H_2O$ 0.1M. After 2 hours, the $CaCl_2 2H_2O$ 0.1M solution was replaced with a new one. Two samples were prepared for every condition. The samples stayed in the $CaCl_2$ for 3 days prior to mechanical measurements.

Alginate+EDC/NHS+Long Coral Collagen Fibers Samples:

~15 cm of dialysis membrane was washed in DDW. One side of the membrane was tied. 10 µl of EDC+10 µl of NHS were mixed in an eppendorff tube. About 7 long fiber bundles (with approximately 200 µm in overall width for each bundle) were inserted into the membrane. Off-axis orientations of the bundles were obtained at the final stage of the composite samples). The EDC/NHS solution was added to the membrane and 3 ml of alginate were added to the dialysis tube and mixed mechanically. An additional tie was made at the open side. The full tube was inserted to 15 ml tube filled with $CaCl_2 2H_2O$ 0.1M. After 2 hours, the $CaCl_2 2H_2O$ 0.1M solution was replaced with a new one. Two samples were prepared for every condition. The samples stayed in the $CaCl_2$ for 3 days prior to mechanical measurements.

Tension Testing:

The samples which were tested were cylindrical shaped, 4 mm long and 5.7 mm in diameter. They were held in the Instron loading frame machine. The experiments were recorded with an optical digital image correlation DIC system to make sure that no sliding occurred during the tests between the edges of the cylindrical sample and the machine. No sliding was detected. The tensile zone of the samples between the machine grippers was about 13 mm.

Results

Photographs of the control and collagen comprising alginate composites are provided in FIGS. 19 and 20.

FIG. 22 shows the stress versus strain of a bio-composite cross-linked collagen with alginate hydrogel along with the stress-strain response of the control sample without fibers. The results clearly show that the addition of 7 collagen fiber bundles with very low overall fiber volume fraction has increased the mechanical resistance and the absorbed energy in the material (area under closed load cycle). It is important to note that the same cross-linker used for the fibers was added in the control sample to account for a self matrix cross-linking effect.

Example 9

Long Stretched and Bundled Collagen Fibers Cross-Linked with Sodium Alginate Hydrogel: Collagen-NHS-Alginate-on Axis Orientation Materials and Methods Alginate+EDC/NHS (Control Samples):

5 cm of dialysis membrane was washed in DDW. One side of the membrane was clipped. 10 µl of EDC+10 µl of NHS were mixed in an eppendorff tube. The EDC/NHS solution and 3 ml of 5% w/v sodium alginate was inserted to the membrane tube and mixed mechanically. The open side of the dialysis tubing was clipped. The filled tube was inserted into a 50 ml tube filled with $CaCl_2 2H_2O$ 0.1M. Following 2 hours, the $CaCl_2 2H_2O$ 0.1M solution was replaced with a new one. Two samples were prepared. The samples remained in the $CaCl_2$ for 5 days prior to mechanical measurements.

Alginate+EDC/NHS+Long Coral Collagen Fibers Samples:

5 cm of dialysis membrane was washed in DDW. One side of the membrane was clipped. Bundles of 1.5-2 mm of coral collagen fibers were inserted into the dialysis tube. 20 µl of EDC+20 µl of NHS were mixed in an eppendorff tube. The EDC/NHS solution and 3 ml of 5% w/v sodium alginate was inserted to the membrane tube and mixed mechanically. The open side of the dialysis tubing was clipped. The filled tube was inserted into a 50 ml tube filled with $CaCl_2 2H_2O$ 0.1M. Following 2 hours, the $CaCl_2 2H_2O$ 0.1M solution was replaced with a new one. One sample was prepared. The sample remained in the $CaCl_2$ for 5 days prior to mechanical measurements. The cross section area of the fibers in alginate matrix was 7.7-13% (for 1.5-2 mm diameter coral collagen bundle in 5.7 mm alginate diameter).

Results

A photograph of the composite is provided in FIG. 24.

The graphs presented in FIGS. 25 and 26 indicate that the EDC/NHS crosslinker strengthens the coral collagen bundle in comparison to the other samples.

Example 10

Chitosan-Genipin-Coral Collagen Fibers Crosslinking

Materials and Methods

Chitosan mid viscosity solution (Sigma) 2% w/v was prepared in acetic acid 1%, chitosan high-mid (1:1 ratio) viscosity solution 2% w/v was prepared in acetic acid 1%. Air bubbles were removed using vacuum oven.

2.5 ml of Chitosan solution were poured to cylindrical Teflon mold. 2 samples of mid viscosity chitosan and 2 samples of mid-high viscosity chitosan were prepared. 50 ul of genipin crosslinker (Sigma) 50 mg/ml were added to the chitosan. Chopped coral fibers were added to 2 of the 4 samples (one mid viscosity sample and one mid-high viscosity sample). After 48 hrs at RT—the samples became Dark blue hydrogel, 2 of them crosslinked with chopped coral collagen fibers.

Results

A firm chitosan hydrogel crosslinked with chopped coral fibers using genipin crosslinker was created.

FIGS. 28 and 29 are photographs of representative samples of the composites.

Example 11

Extraction of Collagen Fibers from Soft Coral

Soft coral *Sarcophyton ehrenbergi* colony was reaped from the Indo-Pacific octocoral and kept frozen in −20° C. freezer. Coral colony was thawed 24 hours prior to fiber extraction. A small piece of the coral was manually removed from the rest of the colony. The piece was cut into two parts which were removed slowly in different directions in order to pull the coral fibers from the coral mesoglea. The fibers were bound several times around a U shaped frame (30×40×30 mm) in an oriented parallel shape as seen in FIG. 30. The U shaped apparatus with the fibers, were washed with DDW and 70% Ethanol and manually cleaned, removing coral cell debris and residues. The fibers were kept in 70% ethanol at 4° C. before biocomposite fabrication.

Results

Coral fibers were extracted from the coral and aligned parallel on a metal frame as seen in FIG. 30. Most of the fibers were aligned parallel in the tensile direction. However, some of the fibers were aligned at an angle in comparison to the major fiber group and the loading direction. They were aligned off axis and since they were loaded at an angle they will produce lower tensile strength in comparison the 0° angle.

This extraction method enables simple handling of the fibers and an option to control the direction and length of fibers which are inserted to the biocomposite. Furthermore, it saves the coral fibers from being stretched inside the composite during its fabrication and allows matrix gelation with maximum surface area of the fibers exposed to the crosslinker and the hydrogel.

Example 12

Fabrication of an Alginate Collagen Biocomposite

A thin rectangular film was made from Alginate (Protanal 10-60LF 3% w/v by FMC biopolymers) w/v in DDW. Alginate type was Protanal 10-60LF 3% w/v.

Figure 31A:
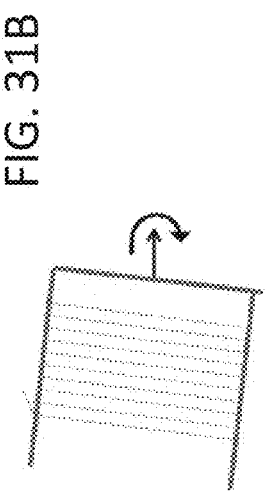
Figure 31C:
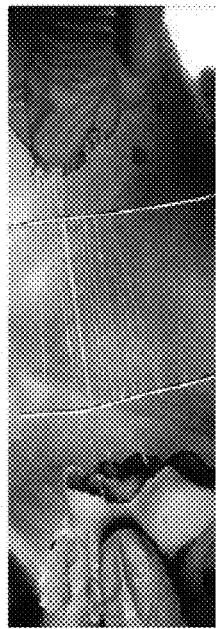
Figure 31B:
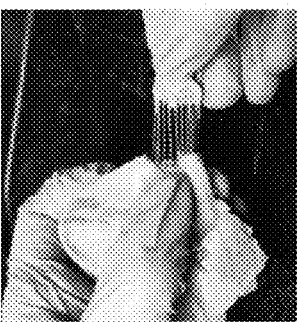
Figure 31D:
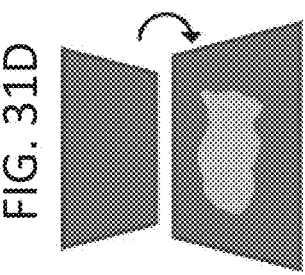
Figure 31E:
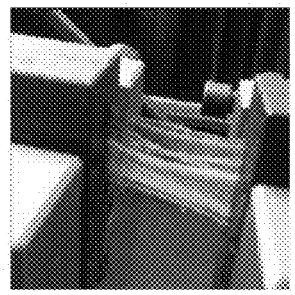

Coral collagen fibers were extracted from the coral mesoglea, wrapped on U shaped isolated wire (described in Example 11) and washed with distilled water and 70% ethanol as seen in FIG. 31C. The volume fraction for the fibers can vary and is easily controlled by adding more wraps of fibers along the metal wire. Dialysis membrane (32 mm diameter, 7 cm length) was washed with distilled water and the fibers apparatus was inserted inside, the fibers aligned parallel to the membrane direction. One side of the membrane was sealed. Mixture of 1:1 EDC:NHS crosslinker 1M was prepared and inserted in to the membrane and manually mixed with the fibers. The crosslinker is used for the binding of alginate-collagen and collagen-collagen. 3 ml of alginate solution were also inserted to the membrane, air bubbles were removed, and the other side of the membrane was sealed. The total concentration of the crosslinker in the alginate solution was 45 mM. The membrane was placed in a petri dish with a flat weight placed above to flatten the biocomposite as schematically illustrated in FIG. 31D. 0.1M $CaCl_2$ solution was poured into the plate, for ionic gelation of the alginate. After 48 hours the gelation was completed and dialysis membrane could be removed. The complete bio-composite is shown in FIG. 31E.

Results

The rectangular sheet biocomposite consists of long (30-40 mm) coral collagen fibers, aligned parallel and crosslinked to thin alginate hydrogel film. The dimensions ranged between 0.3 mm-1.1 mm thickness, 15-20 mm width and 30-40 mm length.

The fabrication method facilitated the fibers handling and the orientation control. Although the manual production created non homogenous areas, most of them were removed before the mechanical testing. The resulting composites were transparent with clear, separate fibers oriented unidirectional as seen in FIG. 31E. However, not all fibers bundles were aligned in the loading direction.

The composites were firm and didn't dehydrate during measurements in the open air for several hours due to the hydrogel's large water content. The alginate hydrogel provided humid surrounding for the collagen fibers, yet, between measurements the samples were kept in 0.1M $CaCl_2$ solution.

Mechanical tension results clearly demonstrate that the collagen fibers have significantly reinforced the alginate matrix in comparison to the matrix alone. FIG. 32 shows two stress-strain plots, one of stretch to failure measurements for the matrix-alone material system (control) in comparison to mechanical response of the current fabricated biocomposite. Ultimate tensile strength for the biocomposite is about 30 times higher than the matrix alone. Furthermore, alginate matrix behavior was linear and the added collagen fibers have completely rendered the composite behavior to a hyperelastic-type common in tissue materials and significant increase in strength with larger elongation and load bearing capacities. In addition cyclic testing was also performed and the results are plotted in FIG. 33. These measurements are also compared with the hyperelastic behavior of the matrix-alone (control). The results support the previous static tests in terms of the added cyclic elasticity by the collagen to the new fabricated biocomposite material.

The tensile stress of the matrix alone was found to be 25 kPa (for this specific sample) at 13% strain, for the biocomposite 1.1 MPa at 28% strain. Most of the samples were not stretched to failure but in cyclic mode up to 10% strain.

Example 13

Biocomposite with Organized Orientations of Fibers

The aim of this example was to demonstrated controlled manufacturing ability of the fiber systems, with different combinations of volume and organized orientations. Therefore, three biocomposite systems were fabricated. Initially the collagen fibers were extracted and organized with pre-specified orientations and geometry as shown in FIG. 34. These three configurations (left to right in FIG. 34) include: 1) cross-ply 0/90° fibers, 2) angle-plied±33° and 3) aligned unidirectional)(0° mounted on stainless steel wire frames. Of note, these basic orientations can be spatially rotated to generate different combinations of angles and systems. For example, it is possible to rotate the cross-play system to generate a new ±45° orientation and be used with other layers having different orientations.

Next, biocomposites were produced from these fiber systems using the fabrication process described in Example 12. FIGS. 35A-C shows the corresponding composite with the embedded fibers. These samples were cut for mechanical testing.

Mechanical tests were carried out at 1 mm/min strain. The second and third samples were tested twice with 4 cycles up to 10% strain. FIG. 37 shows the cyclic performance of the biocomposites with organized fiber systems. All the three samples were then tested statically (monotonically) and taken to failure. FIG. 38 shows a range of mechanical response controlled by the fiber orientations.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated composite comprising bundles of collagen fibers embedded in a matrix, said collagen fibers being isolated from a *Sarcophyton* sp. coral, and said matrix comprising a material selected from the group consisting of a polysaccharide, a polypeptide, polylipid, a synthetic polymer, a metal and a mineral, wherein said bundle of collagen fibers comprise woven fibers, twisted fibers, braided fibers, knitted fibers, tied fibers, or sutured fibers.

2. A wire composed of the composite of claim 1.

3. The composite of claim 1, wherein at least a portion of said first component and a portion of said second component are crosslinked.

4. A method of generating the collagen composite of claim 1, comprising:
    (a) manipulating said collagen fibers of said *Sarcophyton* sp. coral to generate a bundle of collagen fibers; and
    (b) contacting said bundle of collagen fibers with said second component, thereby generating the collagen composite of claim 1.

5. The method of claim 4, wherein said manipulating is selected from the group consisting of weaving, twisting, braiding, knitting, tying and suturing.

6. The method of claim 4, further comprising crosslinking said composite following said contacting.

7. The method of claim 4, further comprising freeze-drying said composite following said contacting.

8. An implantable device comprising the composite of claim 1.

* * * * *